United States Patent
Huang et al.

(10) Patent No.: US 11,124,571 B2
(45) Date of Patent: Sep. 21, 2021

(54) METHODS OF SENSITIZING CANCER TO IMMUNOTHERAPY

(71) Applicant: CASE WESTERN RESERVE UNIVERSITY, Cleveland, OH (US)

(72) Inventors: Alex Yee-Chen Huang, Cleveland, OH (US); Agne Petrosiute, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 16/303,846

(22) PCT Filed: May 24, 2017

(86) PCT No.: PCT/US2017/034285
§ 371 (c)(1),
(2) Date: Nov. 21, 2018

(87) PCT Pub. No.: WO2017/205514
PCT Pub. Date: Nov. 30, 2017

(65) Prior Publication Data
US 2019/0194330 A1 Jun. 27, 2019

Related U.S. Application Data

(60) Provisional application No. 62/341,459, filed on May 25, 2016, provisional application No. 62/432,131, filed on Dec. 9, 2016.

(51) Int. Cl.
C07K 16/28 (2006.01)
C12N 9/12 (2006.01)
(Continued)

(52) U.S. Cl.
CPC .... *C07K 16/2827* (2013.01); *A61K 39/39541* (2013.01); *A61P 35/00* (2018.01); *C07K 14/70596* (2013.01); *C12N 9/12* (2013.01); *C12Y 207/11022* (2013.01); *A61K 38/00* (2013.01); *A61K 45/06* (2013.01)

(58) Field of Classification Search
None
See application file for complete search history.

(56) References Cited

U.S. PATENT DOCUMENTS

2012/0010229 A1   1/2012   MacDougall et al.
2018/0185381 A1*  7/2018   Rutka .................... A61K 31/55

FOREIGN PATENT DOCUMENTS

WO   2013/188355 A1   12/2013
WO   2015/026634 A1    2/2015
WO   2015026634       *  2/2015

OTHER PUBLICATIONS

Lockwood WW, et al. DNA amplification is a ubiquitous mechanism of oncogene activation in lung and other cancers. Oncogene. 2008; 27:4615-4624 (Year: 2008).*

(Continued)

*Primary Examiner* — Karl J Puttlitz
(74) *Attorney, Agent, or Firm* — Tarolli, Sundheim, Covell & Tummino LLP

(57) ABSTRACT

A method of sensitizing cancer to immunotherapy in a subject in need thereof includes administering to the subject a therapeutically effective amount of a CdK5 inhibitor to suppress immune checkpoint PD-L1.

9 Claims, 19 Drawing Sheets

Specification includes a Sequence Listing.

(51) Int. Cl.
*C07K 14/705* (2006.01)
*A61K 39/395* (2006.01)
*A61P 35/00* (2006.01)
*A61K 38/00* (2006.01)
*A61K 45/06* (2006.01)

(56) References Cited

OTHER PUBLICATIONS

Harada T, et al. Genome-wide DNA copy number analysis in pancreatic cancer using high-density single nucleotide polymorphism arrays. Oncogene. 2008; 27:1951-1960 (Year: 2008).*

Eggers JP, et al. Cyclin-dependent kinase 5 is amplified and overexpressed in pancreatic cancer and activated by mutant K-Ras. Clin Cancer Res. 2011; 17:6140-6150. (Year: 2011).*

Choi HS, et al. Single-nucleotide polymorphisms in the promoter of the CDK5 gene and lung cancerrisk in a Korean population. J Hum Genet. 2009; 54:298-303. (Year: 2009).*

Kibel AS, et al. Genetic variants in cell cycle control pathway confer susceptibility to aggressive prostate carcinoma. The Prostate. 2016; 76:479-490. (Year: 2016).*

Wei K, et al. An immunohistochemical study of cyclin-dependent kinase 5 (CDK5) expression in non-small cell lung cancer (NSCLC) and small cell lung cancer (SCLC): a possible prognostic biomarker. World J Surg Oncol. 2016; 14:34 (Year: 2016).*

Meder L, et al. NOTCH, ASCL1, p53 and RB alterations define an alternative pathway driving neuroendocrine and small cell lung carcinomas. Int J Cancer. 2016; 138:927-938. (Year: 2016).*

Liu JL, et al. Cyclin-dependent kinase 5 regulates the proliferation, motility and invasiveness of lung cancer cells through its effects on cytoskeletal remodeling. Mol Med Rep. 2015; 12:3979-3985 (Year: 2015).*

Pozo K, et al. The role of Cdk5 in neuroendocrine thyroid cancer. Cancer Cell. 2013; 24:499-511. (Year: 2013).*

Xie W, et al. Phosphorylation of kinase insert domain receptor by cyclin-dependent kinase 5 at serine 229 is associated with invasive behavior and poor prognosis in prolactin pituitary adenomas. Oncotarget. (Year: 2016).*

Liu JL, et al. Expression of CDK5/p35 in resected patients with non-small cell lung cancer: relation to prognosis. Med Oncol. 2011; 28:673-678. (Year: 2011).*

Liang Q, et al. CDK5 is essential for TGF-beta1-induced epithelial-mesenchymal transition and breast cancer progression. Sci Rep. 2013; 3:2932. (Year: 2013).*

Chiker S, et al. Cdk5 promotes DNA replication stress checkpoint activation through RPA-32 phosphorylation, and impacts on metastasis free survival in breast cancer patients. Cell Cycle. 2015; 14:3066-3078. (Year: 2015).*

Catania A, et al. Expression and localization of cyclin-dependent kinase 5 in apoptotic human glioma cells. Neuro Oncol. 2001; 3:89-98. (Year: 2001).*

Yushan R, et al. Insights into the clinical value of cyclin-dependent kinase 5 in glioma: a retrospective study. World J Surg Oncol. 2015; 13:223. (Year: 2015).*

Zhang X, et al. Aberrant expression of CDK5 infers poor outcomes for nasopharyngeal carcinoma patients. Int J Clin Exp Pathol. 2015; 8:8066-8074. (Year: 2015).*

Cydacel Pharmaceuticals Inc. 2012 Annual Report (Year: 2012).*

CYC065, a Potent Derivative of Seliciclib Is Active In Multiple Myeloma In Preclinical Studies, Abstract, retrieved at https://ashpublications.org/blood/article/116/21/2999/112293/CYC065-a-Potent-Derivative-of-Seliciclib-Is-Active on Oct. 17, 2019 (Year: 2010).*

Li et al., Cancer Genetics 205 (2012) 220-231 (Year: 2012).*

Urashima, et al., British Journal of Cancer (1999), 79(7/8), 1032-1036 (Year: 1999).*

Sabb et al., Molecular Cancer Therapeutics (2006), 5(5), 1299-1308 (Year: 2006).*

* cited by examiner

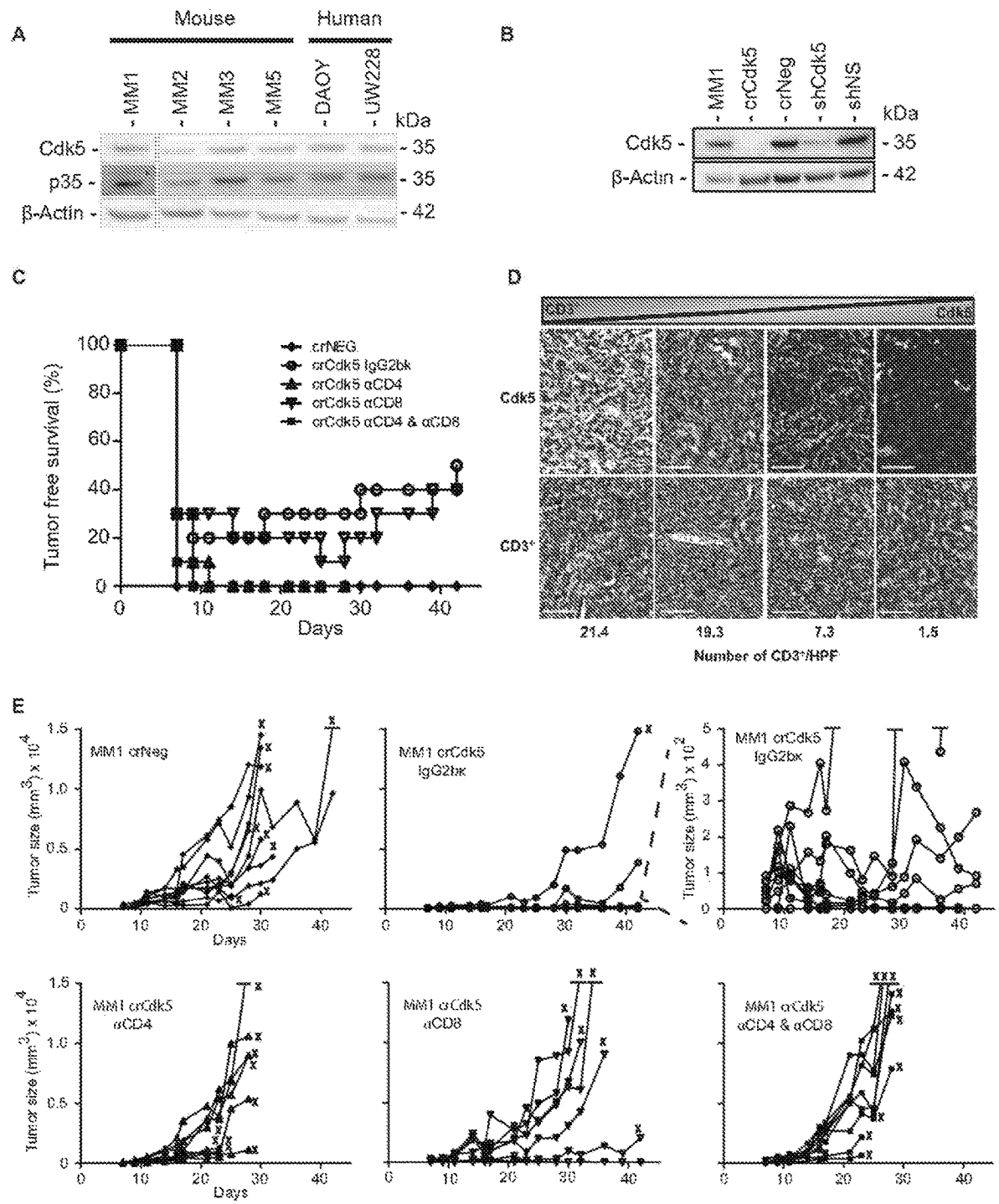
Figs. 1A-E

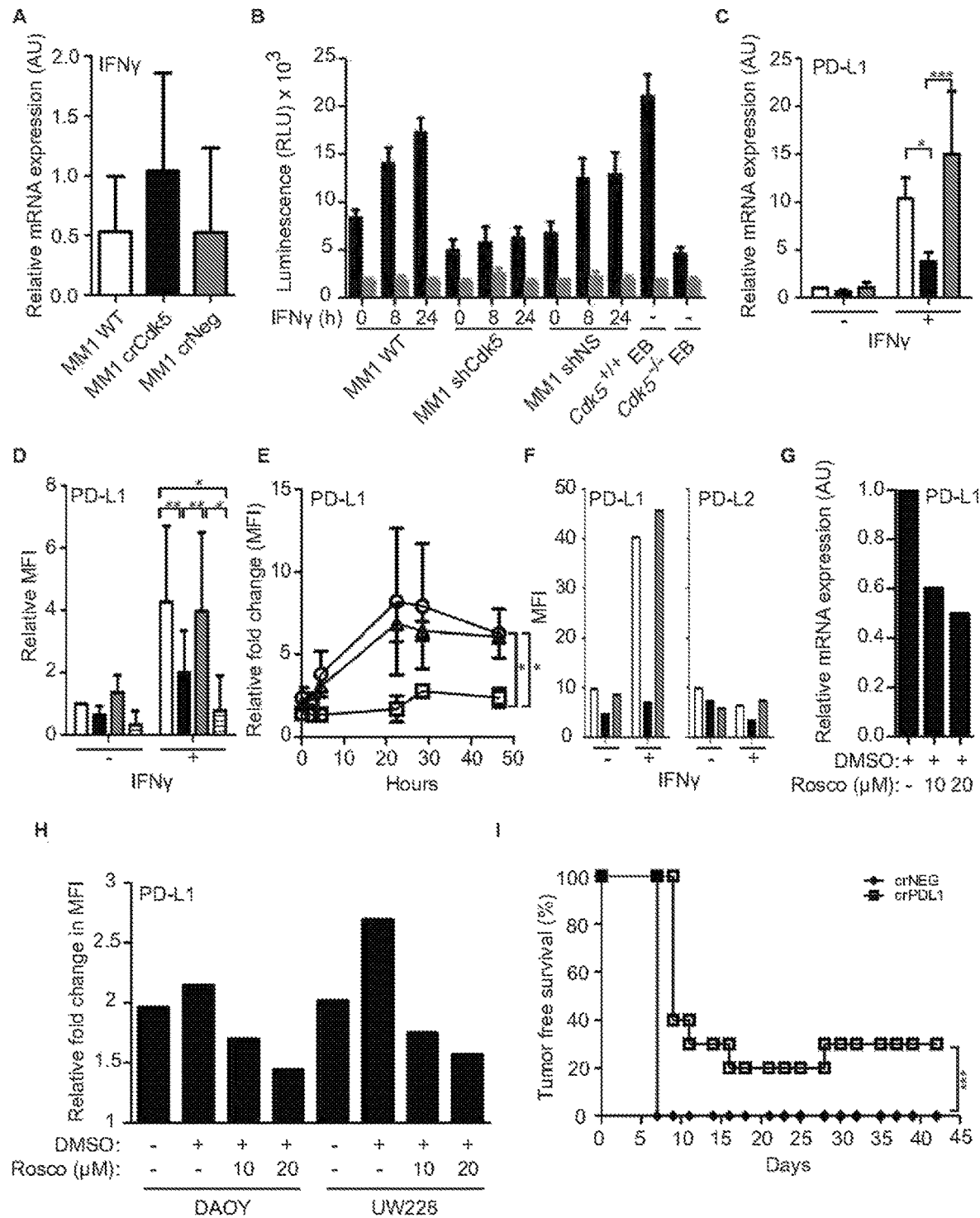
Figs. 2A-I

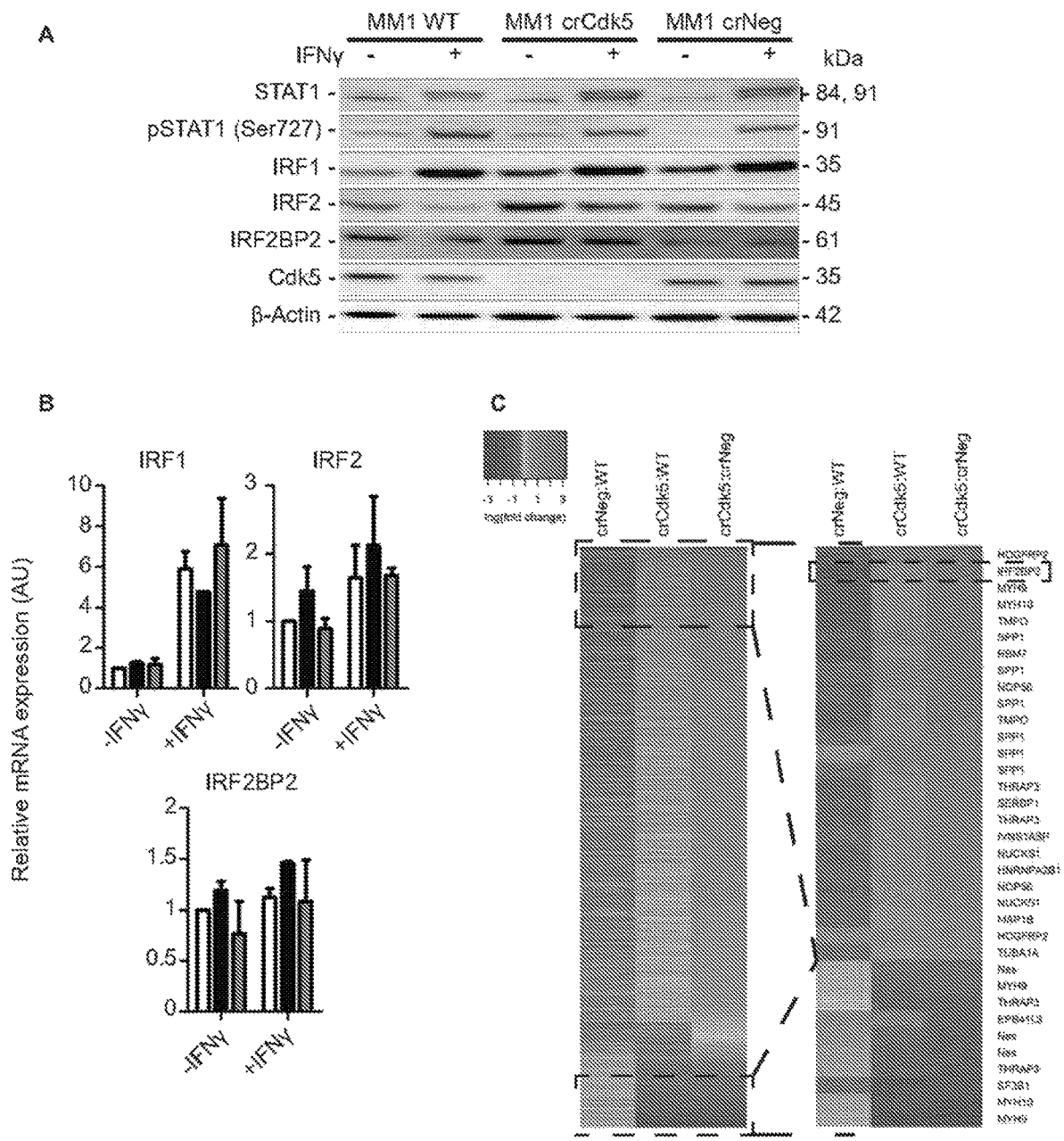
Figs. 3A-C

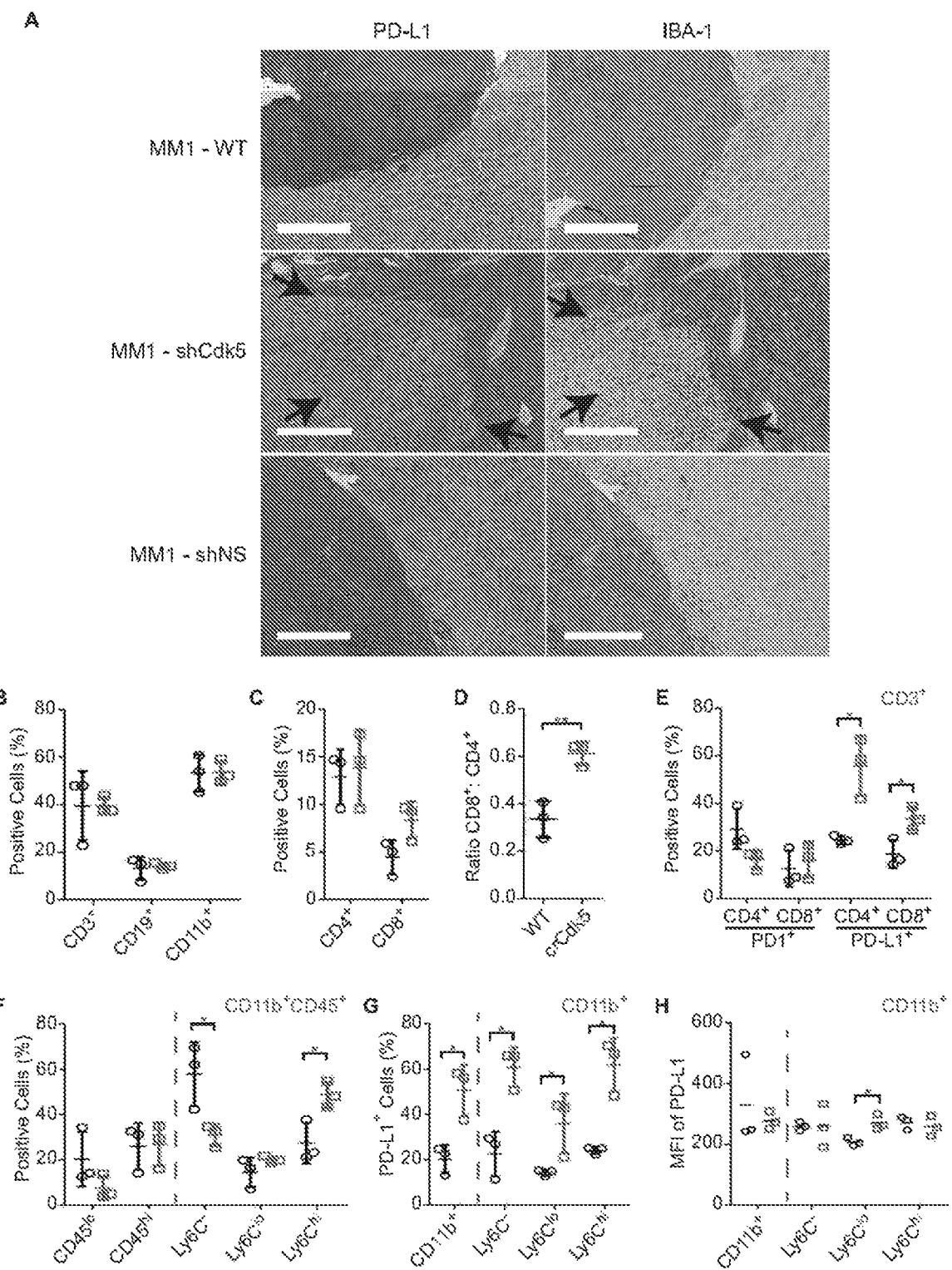
Figs. 4A-H

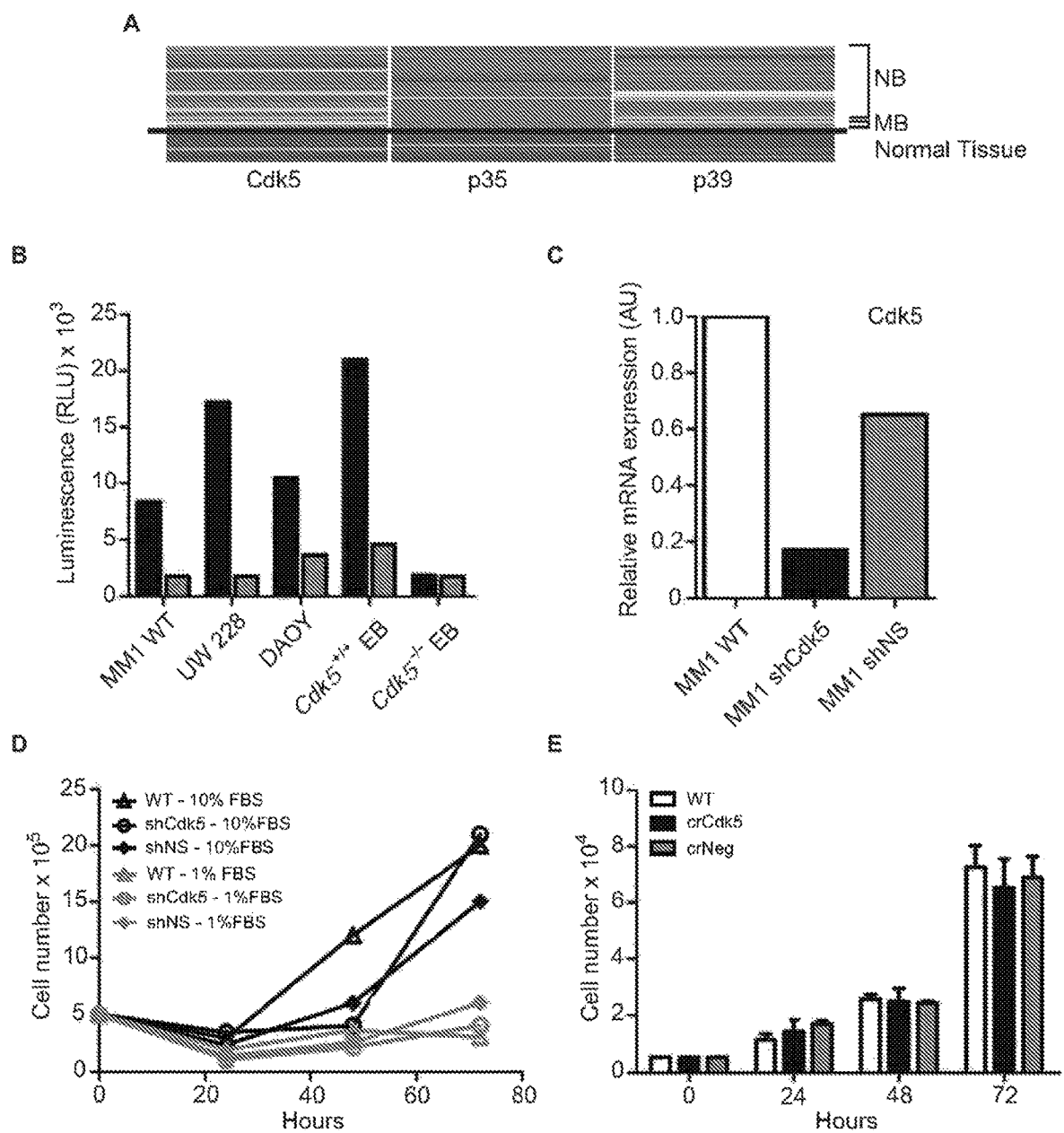
Figs. 5A-E

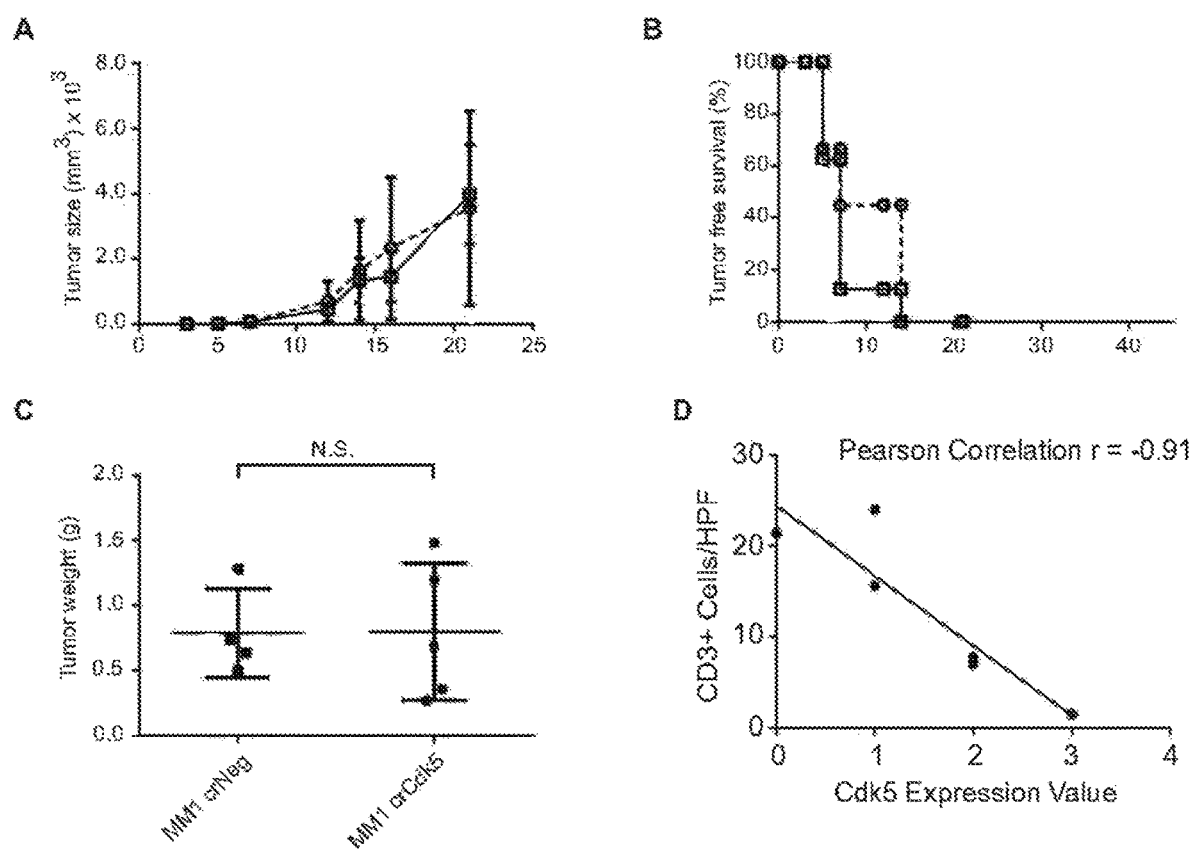
Figs. 6A-D

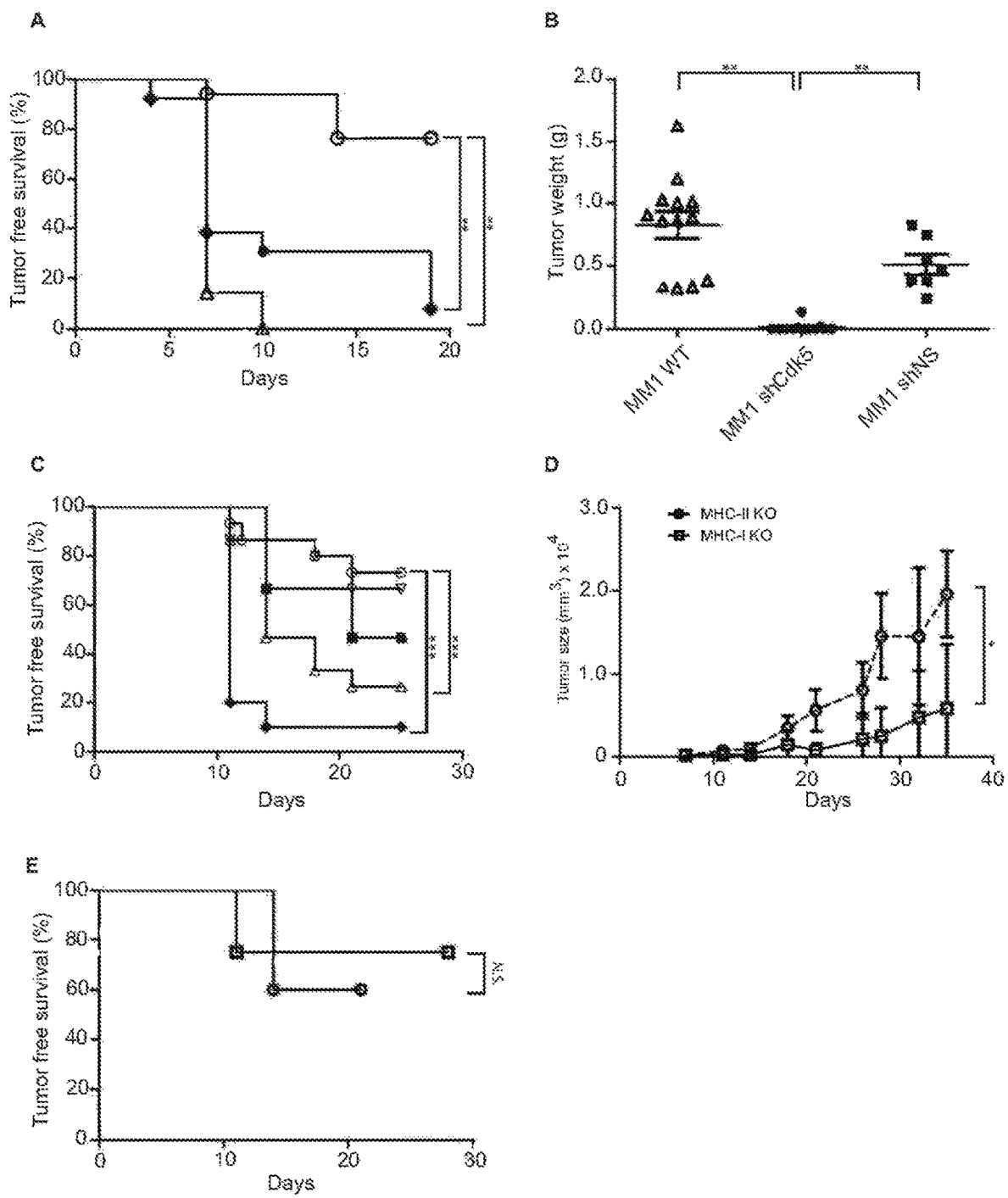
Figs. 7A-E

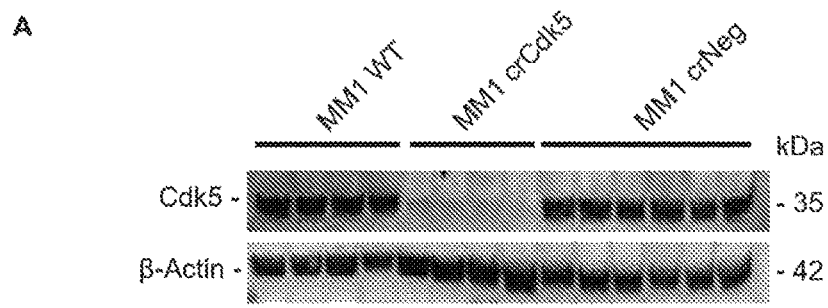
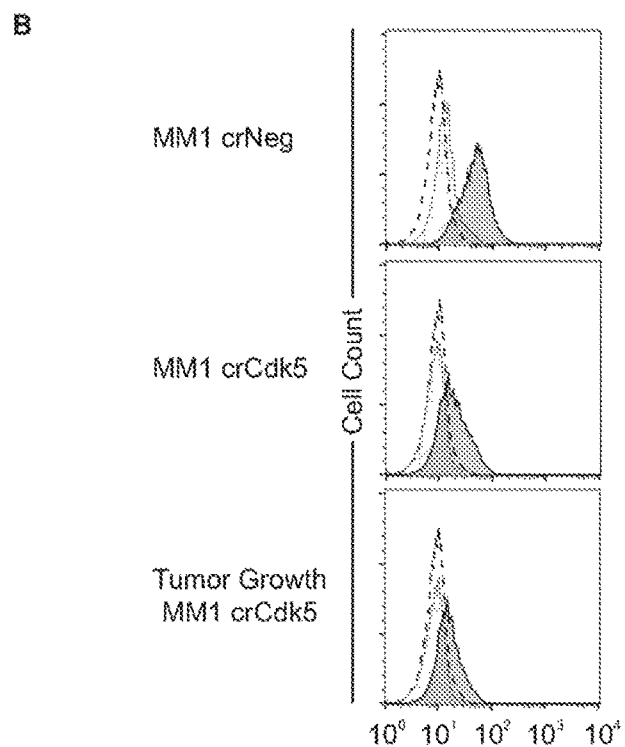
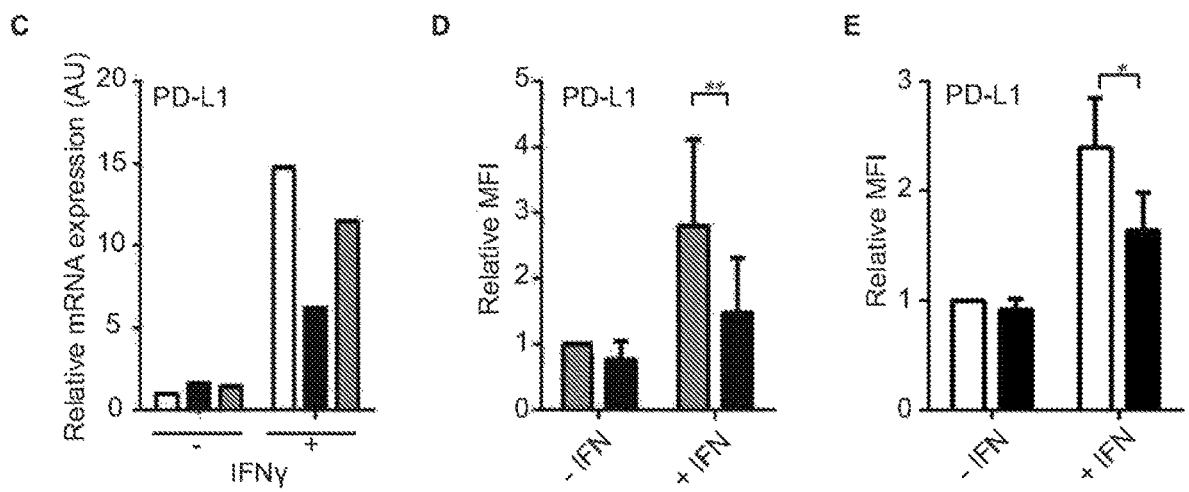
Figs. 8A-E

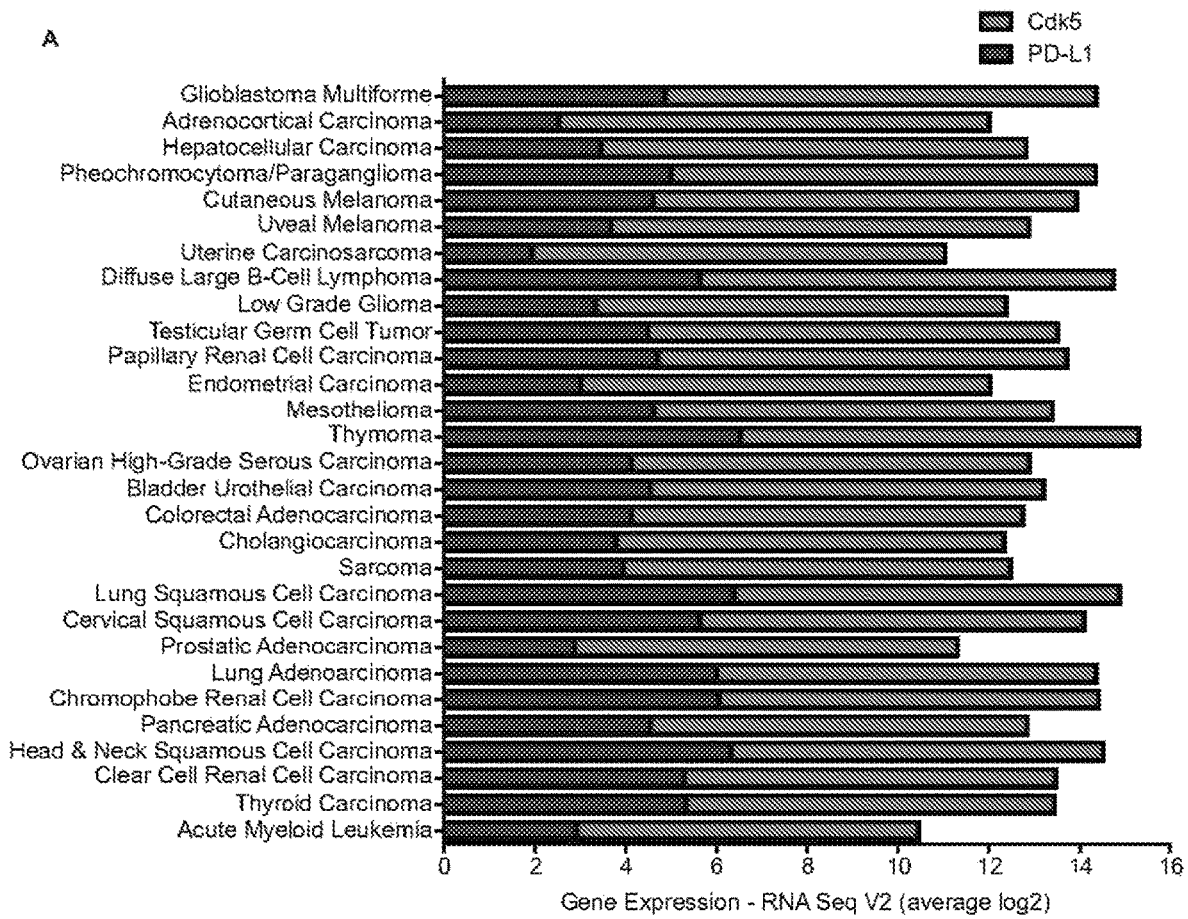
Figs. 9A-B

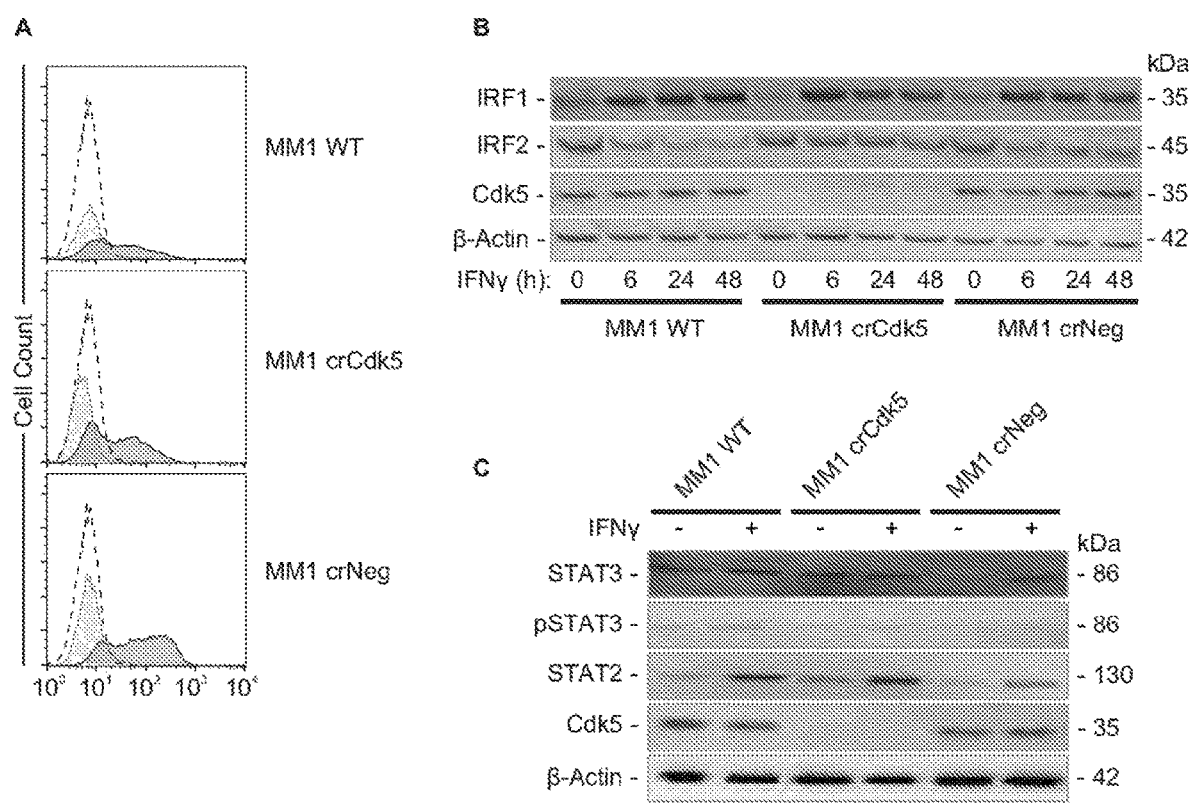
Figs. 10A-C

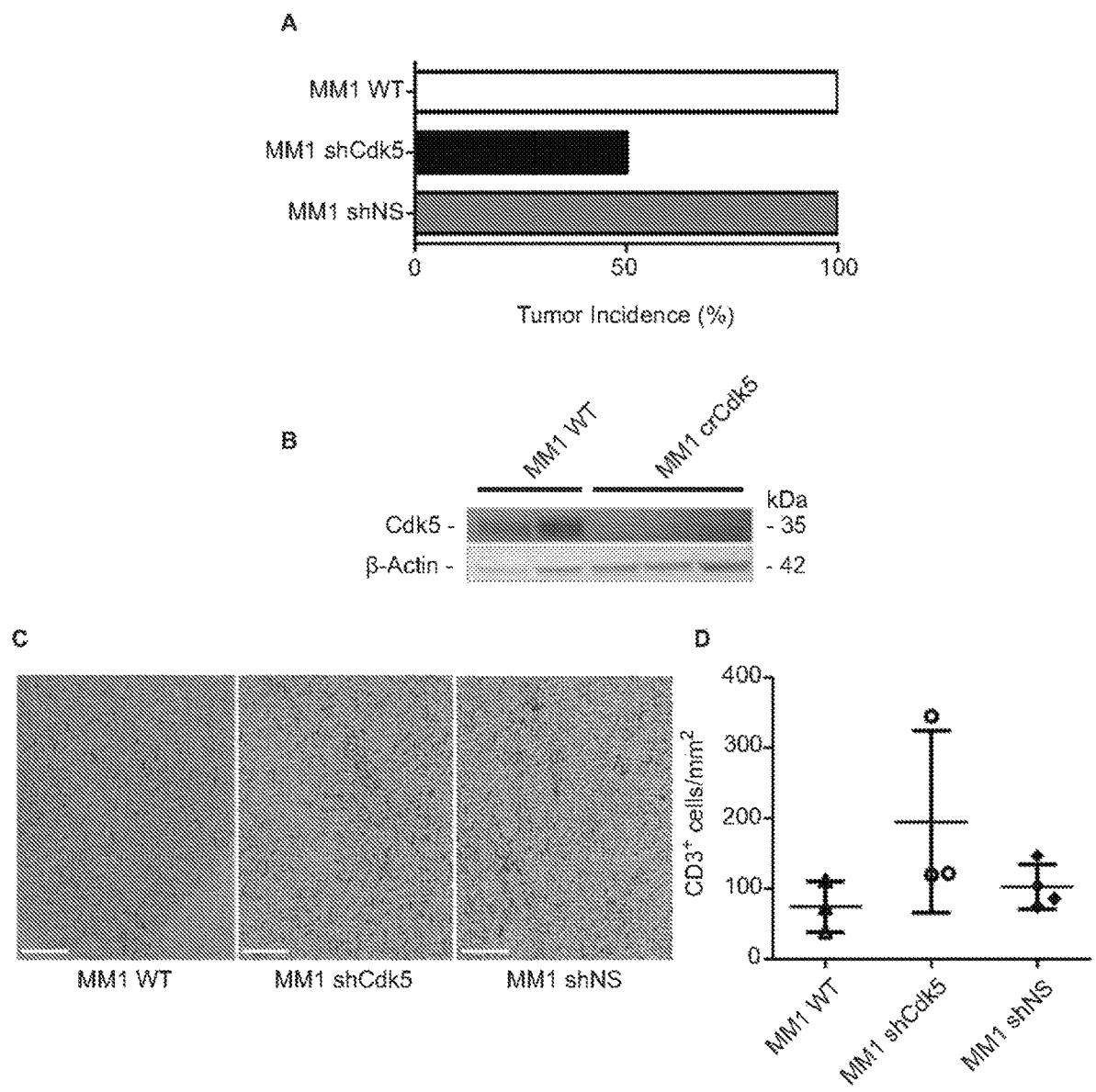
Figs. 11A-D

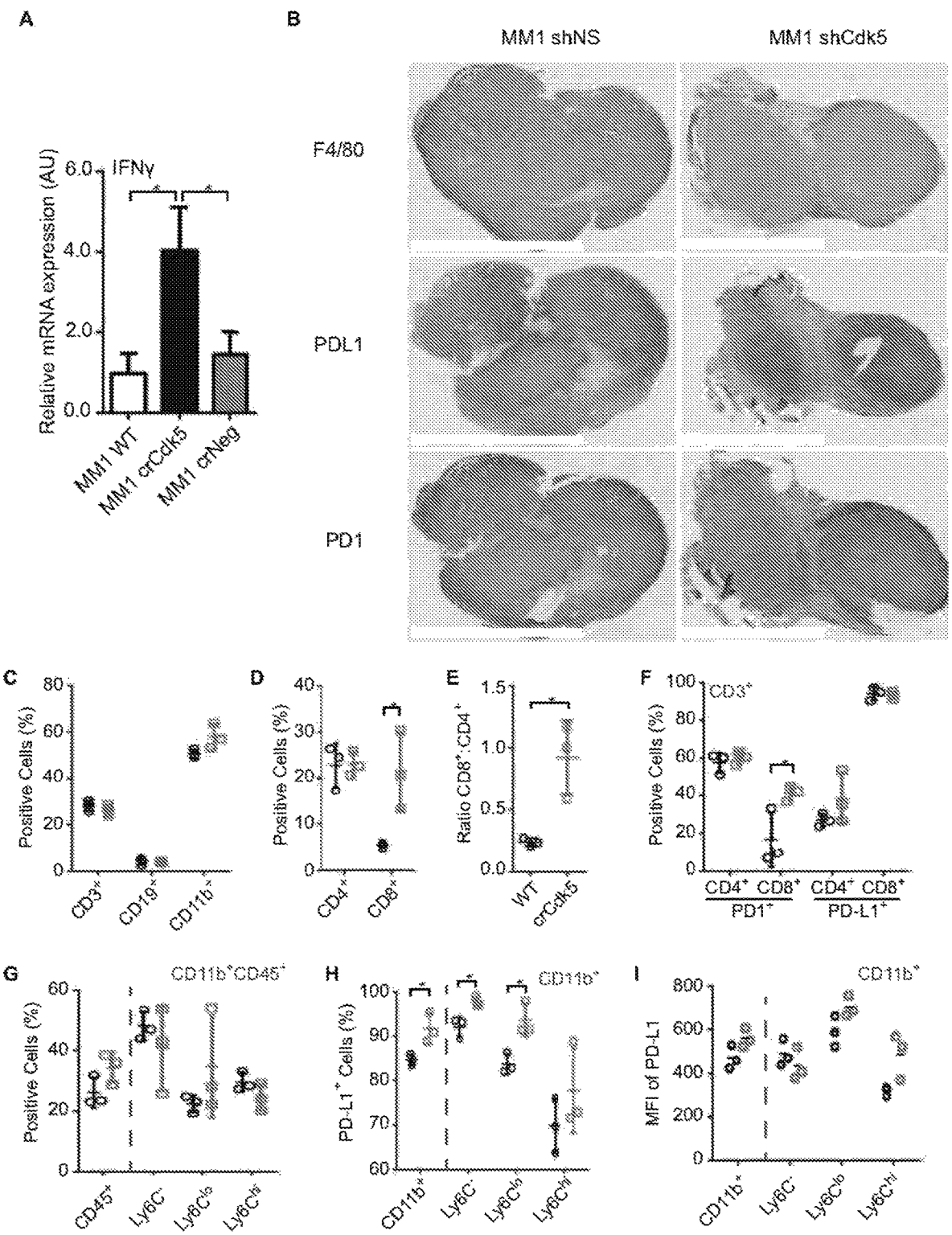
Figs. 12A-I

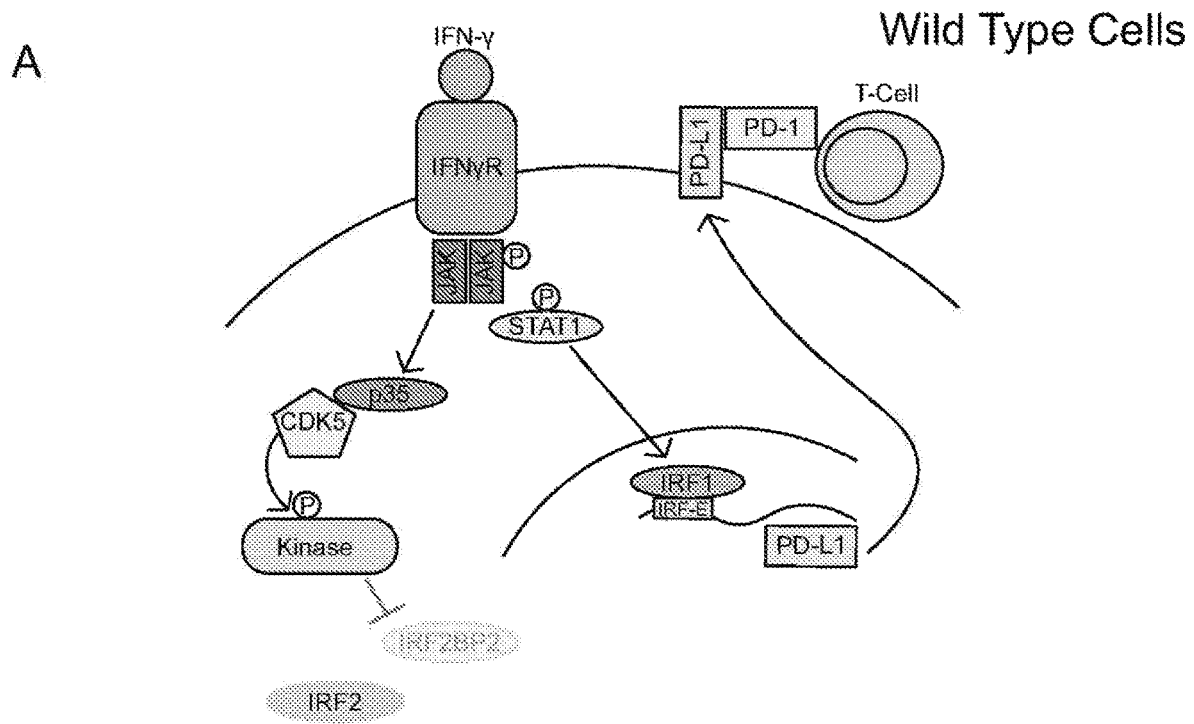
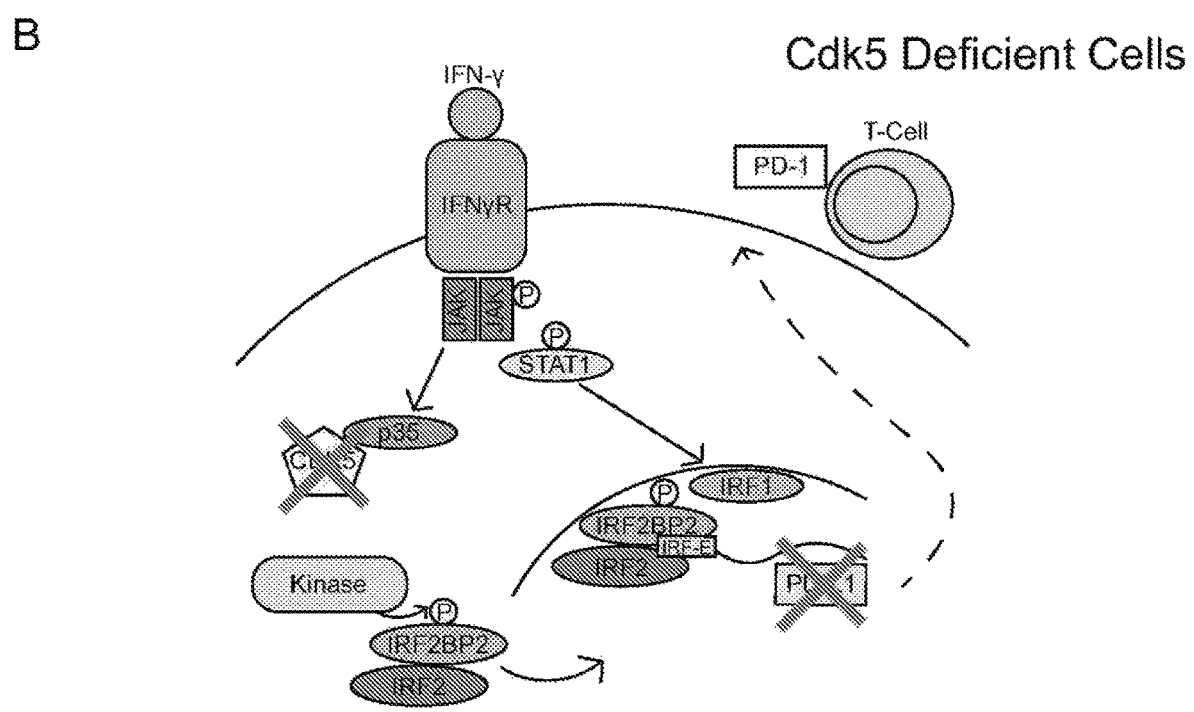
Figs. 13A-B

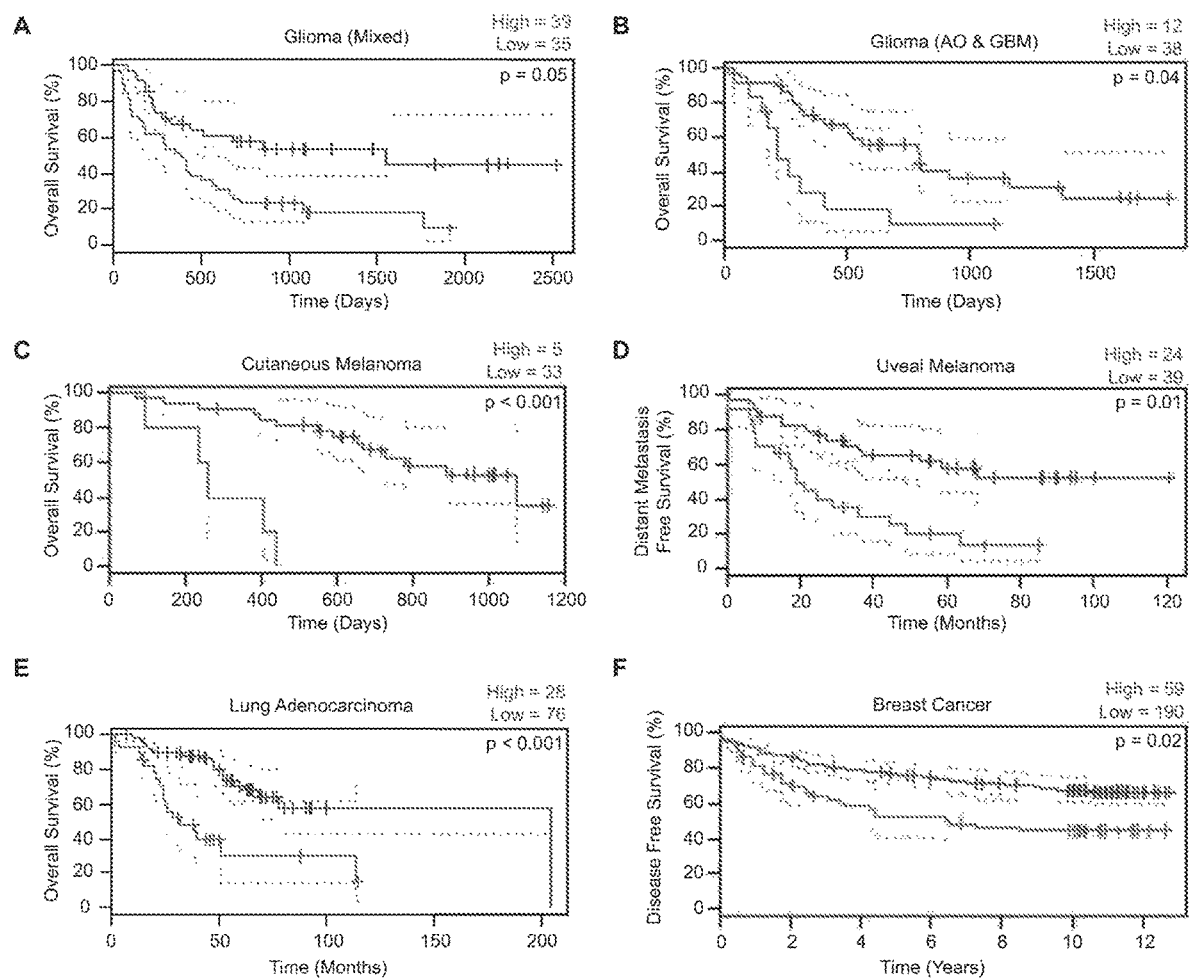
Figs. 14A-F

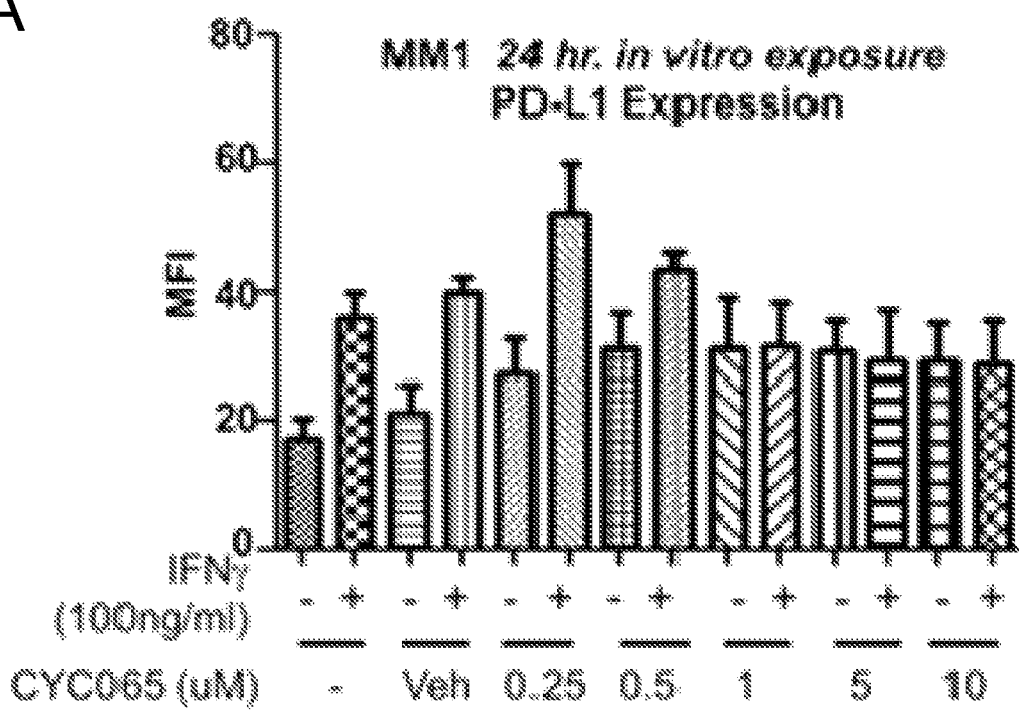
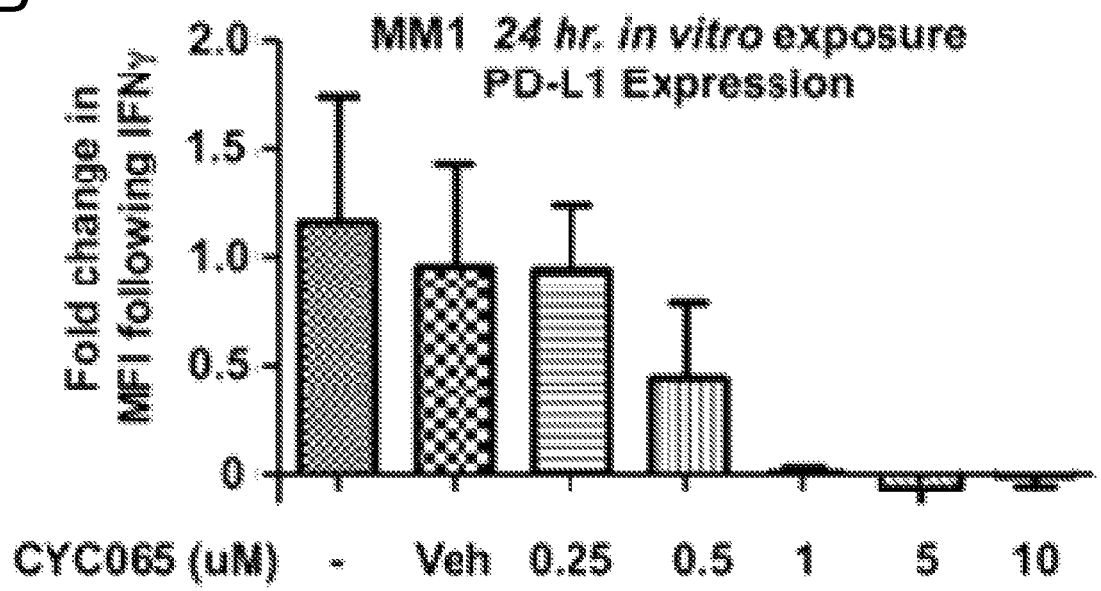
Figs. 15A-B

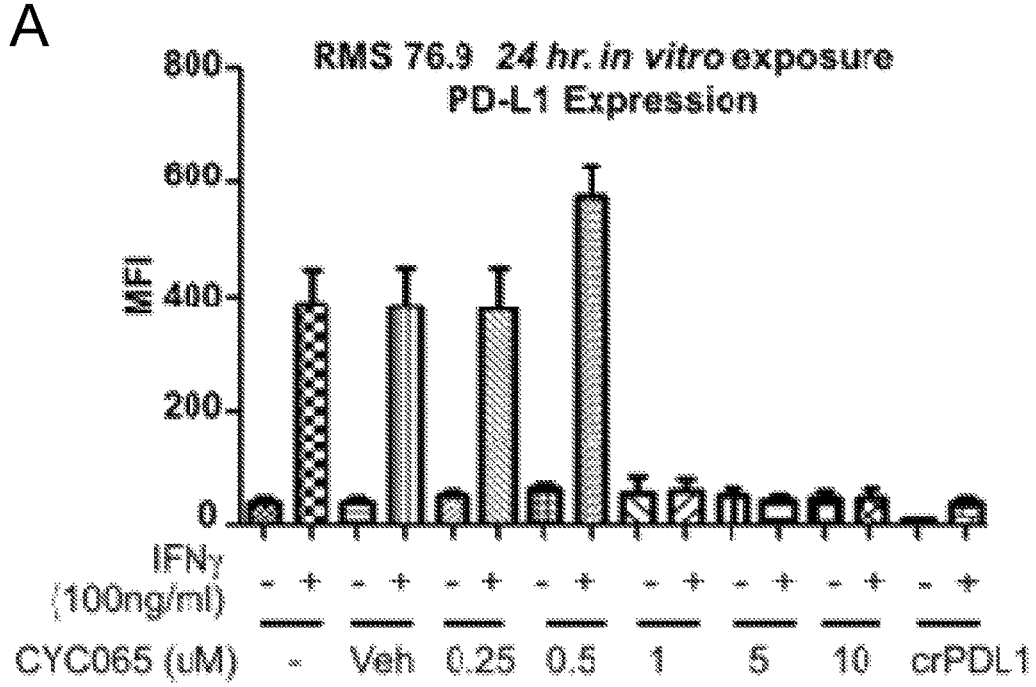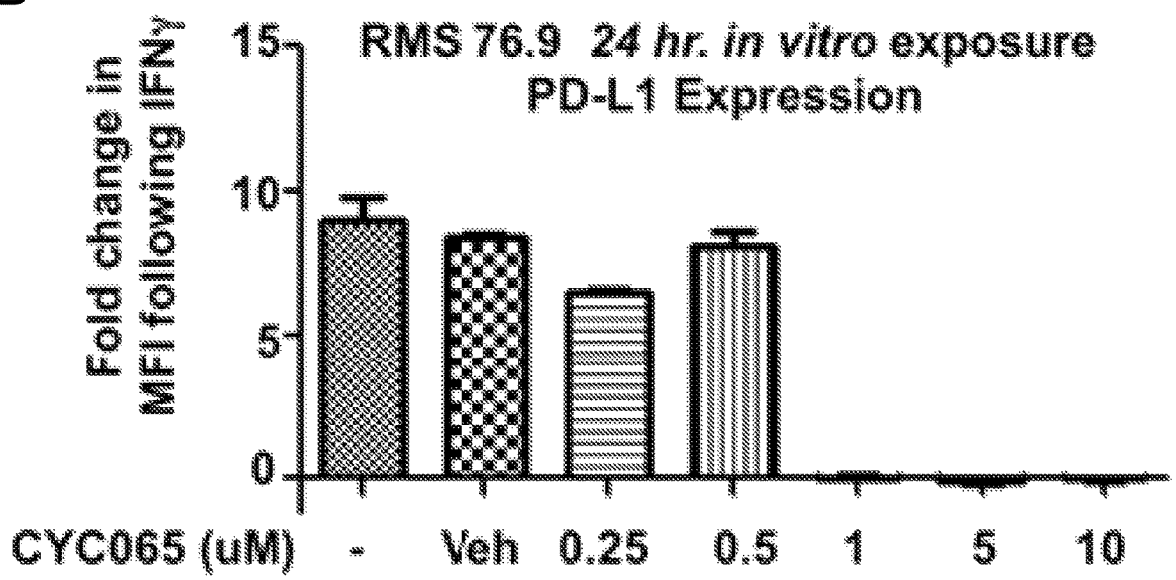
Figs. 16A-B

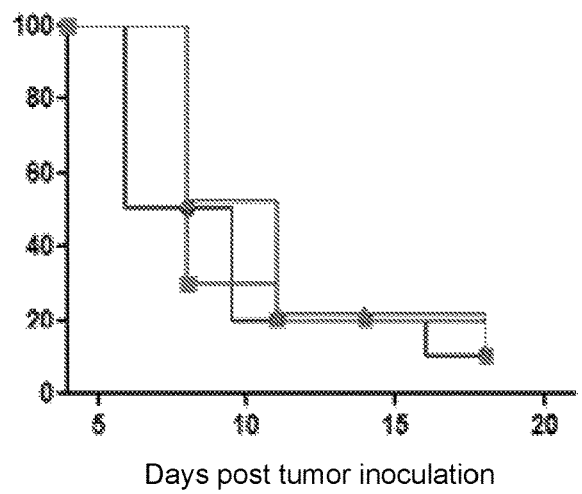
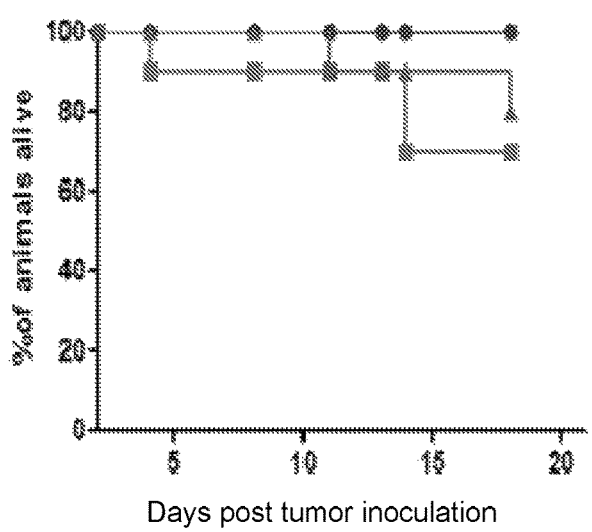
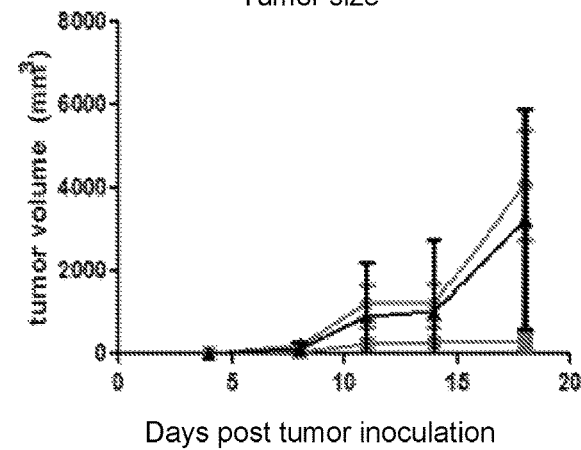
Figs. 17A-C

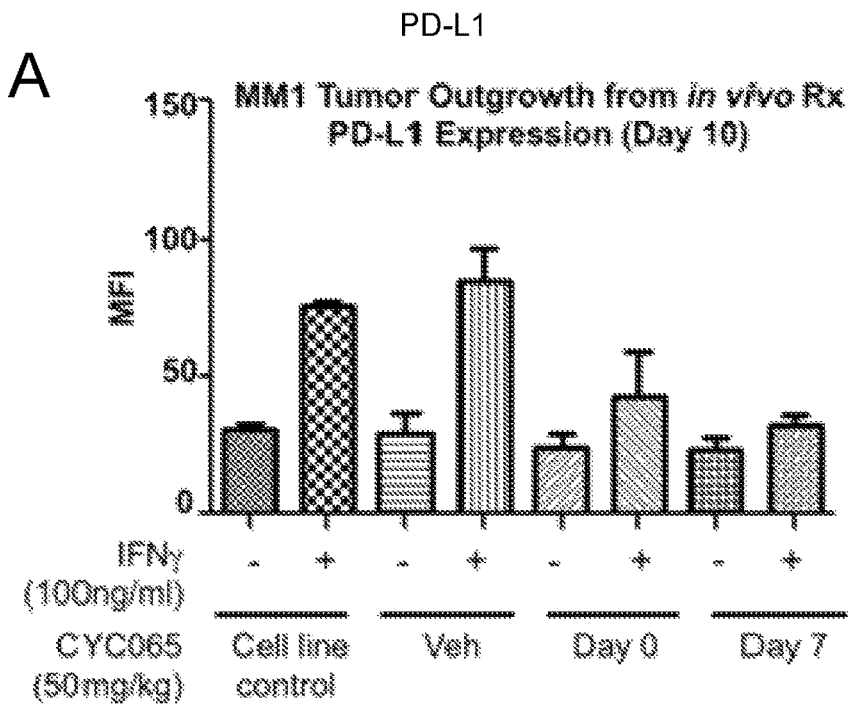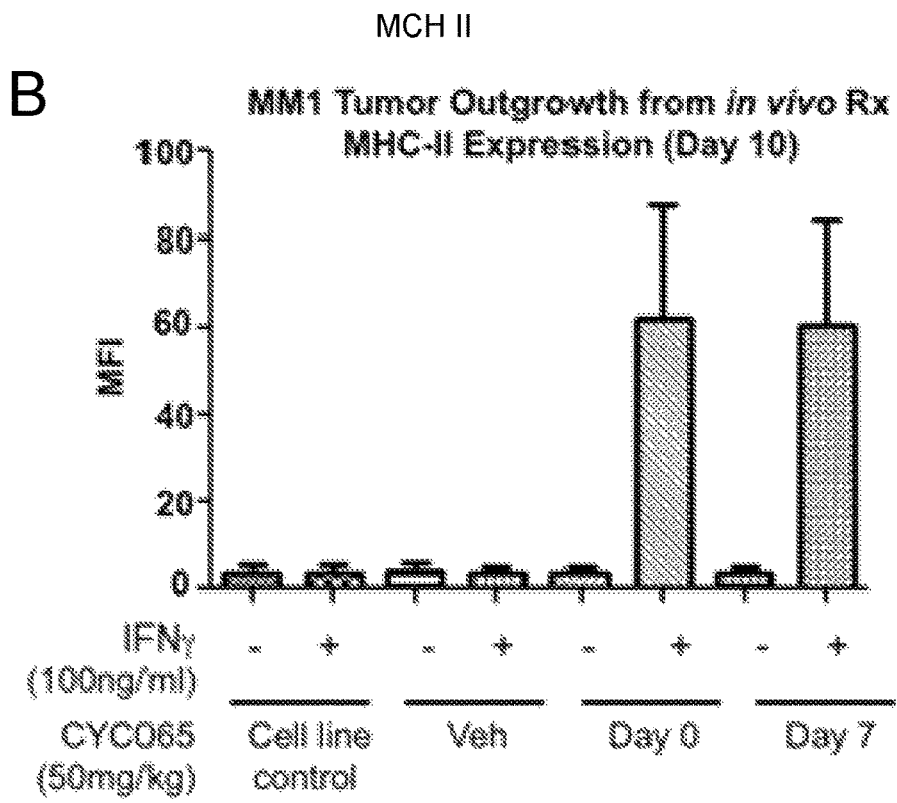
Figs. 18A-B

SEQUENCE LISTING

<160> NUMBER OF SEQ ID NOS: 10

<210> SEQ ID NO 1
<211> LENGTH: 19
<212> TYPE: DNA
<213> ORGANISM: Homo sapiens

<400> SEQUENCE: 1
ttgagtagac agatctccc                                                    19

<210> SEQ ID NO 2
<211> LENGTH: 20
<212> TYPE: DNA
<213> ORGANISM: Homo sapiens

<400> SEQUENCE: 2
ggtccctatg tagcacgttg                                                   20

<210> SEQ ID NO 3
<211> LENGTH: 20
<212> TYPE: DNA
<213> ORGANISM: Homo sapiens

<400> SEQUENCE: 3
gtccatcgac atgtggtcag                                                   20

<210> SEQ ID NO 4
<211> LENGTH: 20
<212> TYPE: DNA
<213> ORGANISM: Homo sapiens

<400> SEQUENCE: 4
ctggtcatcc acatcattgc                                                   20

<210> SEQ ID NO 5
<211> LENGTH: 20
<212> TYPE: DNA
<213> ORGANISM: Homo sapiens

<400> SEQUENCE: 5
ctgccacagc atggattatg                                                   20

<210> SEQ ID NO 6
<211> LENGTH: 20
<212> TYPE: DNA
<213> ORGANISM: Homo sapiens

<400> SEQUENCE: 6
catcatcatt agggccatcc                                                   20

<210> SEQ ID NO 7
<211> LENGTH: 20
<212> TYPE: DNA
<213> ORGANISM: Homo sapiens

<400> SEQUENCE: 7
gtccctatcc cccagctatc                                                   20

<210> SEQ ID NO 8
<211> LENGTH: 20
<212> TYPE: DNA
<213> ORGANISM: Homo sapiens

<400> SEQUENCE: 8

-continued

```
ttcttgtcct tggcgttctt                                              20

<210> SEQ ID NO 9
<211> LENGTH: 20
<212> TYPE: DNA
<213> ORGANISM: Homo sapiens

<400> SEQUENCE: 9
tgctgcataa tcagctacgg                                              20

<210> SEQ ID NO 10
<211> LENGTH: 20
<212> TYPE: DNA
<213> ORGANISM: Homo sapiens

<400> SEQUENCE: 10
tccacggaaa ttctctggtt                                              20
```

METHODS OF SENSITIZING CANCER TO IMMUNOTHERAPY

RELATED APPLICATION

This application claims priority from U.S. Provisional Application Nos. 62/341,459, filed May 25, 2016 and 62/432,131 filed Dec. 9, 2016, the subject matter of which are incorporated herein by reference in their entirety.

GOVERNMENT FUNDING

This invention was made with government support under Grant Nos. P30CA043703, R01CA154656, R21C181875, and UL1TR000439 awarded by The National Institutes of Health. The United States government has certain rights to the invention.

BACKGROUND

Initiation, progression, and completion of the mammalian cell cycle are regulated by various cyclin-dependent kinase (CDK) complexes, which are critical for cell growth. These complexes comprise at least a catalytic (the CDK itself) subunit and a regulatory (cyclin) subunit. Some of the more important complexes for cell cycle regulation include cyclin A (CDK1—also known as cdc2, and CDK2), cyclin B1-B3 (CDK1), cyclin C (CDK8), cyclin D1-D3 (CDK2, CDK4, Cdk5, CDK6), cyclin E (CDK2), cyclins K and T (CDK9) and cyclin H (CDK7). Each of these complexes is involved in a particular phase of the cell cycle.

The activity of CDKs is regulated post-translationally, by transitory associations with other proteins, and by alterations of their intracellular localisation. Tumor development is closely associated with genetic alteration and deregulation of CDKs and their regulators, suggesting that inhibitors of CDKs may be useful anti-cancer therapeutics. Indeed, early results suggest that transformed and normal cells differ in their requirement for e.g., cyclin A/CDK2 and that it may be possible to develop novel antineoplastic agents devoid of the general host toxicity observed with conventional cytotoxic and cytostatic drugs.

The function of CDKs is to phosphorylate and thus activate or deactivate certain proteins, including, for example, retinoblastoma proteins, lamins, histone Hi, and components of the mitotic spindle. The catalytic step mediated by CDKs involves a phospho-transfer reaction from ATP to the macromolecular enzyme substrate. Several groups of compounds (reviewed in N. Gray, L. Detivaud, C. Doerig, L. Meijer, Curr. Med. Chem. 1999, 6, 859) have been found to possess anti-proliferative properties by virtue of CDK-specific ATP antagonism.

Roscovitine is the compound 6-benzylamino-2-[(R)-1-ethyl-2-hydroxyethylamino]-9-isopropylpurine. Roscovitine has been demonstrated to be a potent inhibitor of cyclin dependent kinase enzymes, particularly CDK2. This compound is currently in development as an anti-cancer agent. CDK inhibitors are understood to block passage of cells from the G1/S and the G2/M phase of the cell cycle. Roscovitine has also been shown to be an inhibitor of retinoblastoma phosphorylation and therefore implicated as acting more potently on Rb positive tumors.

Human cancers harbor numerous genetic and epigenetic alterations, generating neoantigens potentially recognizable by the immune system. Although an endogenous immune response to cancer is observed in preclinical models and patients, this response is ineffective, and established cancers are viewed as "self" and tolerated by the immune system. Contributing to this state of tolerance, tumors may exploit several distinct mechanisms to actively suppress the host immune response. Among these mechanisms, endogenous "immune checkpoints" that normally terminate immune responses to mitigate collateral tissue damage can be co-opted by tumors to evade immune destruction. Intensive efforts to develop specific immune checkpoint pathway inhibitors have begun to provide new immunotherapeutic approaches for treating cancer, including the development of the anti-CTLA-4 antibody (Ab), ipilimumab (YERVOY), for the treatment of patients with advanced melanoma.

Programmed Death-1 (PD-1) is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to downregulate T cell activation and cytokine secretion upon binding to PD-1. Unlike CTLA-4, PD-1 primarily functions in peripheral tissues where activated T-cells may encounter the immunosuppressive PD-L1 (B7-H1) and PD-L2 (B7-DC) ligands expressed by tumor and/or stromal cells. Inhibition of the PD-1/PD-L1 interaction mediates potent antitumor activity in preclinical models (U.S. Pat. Nos. 8,008,449 and 7,943, 743), and the use of Ab inhibitors of the PD-1/PD-L1 interaction for treating cancer has entered clinical trials.

SUMMARY

Embodiments described herein relate to a method of sensitizing cancer to immunotherapy or treating tumor immunity in a subject in need thereof by administering to the subject a therapeutically effective amount of a CdK5 inhibitor to suppress immune checkpoint programmed death-ligand 1 (PD-L1) in the cancer cells.

Cancers often evade immune surveillance by adopting peripheral tissue-tolerance mechanisms, such as the expression of programmed cell death ligand 1 (PD-L1), the inhibition of which results in potent antitumor immunity. It was found that cyclin-dependent kinase 5 (Cdk5), a serine-threonine kinase that is highly active in postmitotic neurons and in many cancers, can allow PD-L1 expressing or over-expressing cancers to evade immune elimination. PD-L1 up-regulation can be induced in some cancer cells by Interferon-γ (IFN-γ). Induction of PD-L1 by IFN-γ requires Cdk5. Loss or inhibition of Cdk5 results in persistent expression of the PD-L1 transcriptional repressors, the interferon regulatory factors IRF2 and IRF2BP2, which likely leads to reduced PD-L1 expression on tumors. Accordingly, disruption of Cdk5 activity in the cancer cells with a Cdk5 inhibitor can result in potent CD4(+) T cell-mediated tumor rejection.

In some embodiments, the cancer cells of the subject treated with the Cdk5 inhibitor can express or over-express PD-L1 and/or Cdk5. Cancer cells that express or over express PD-L1 and/or Cdk5 can include medulloblastoma or rhabdomyosarcoma.

In some embodiments the Cdk5 inhibitor can be selected from the group consisting of Dinaciclib, AT7519, Roscovitine, CYCO65, PHA-793887, Milcidib, and SNS-032.

In other embodiments, the method can further include administering a PD-1 binding antagonist and/or a PD-L1 binding antagonist in combination with the Cdk5 inhibitor.

The PD-1 binding antagonist and/or PD-L1 binding antagonist can inhibit PD-1/PD-L1 interaction and/or PD-1/PD-L1 signaling pathway.

In some embodiments, the PD-1 binding antagonist and/or PD-L1 binding antagonist is an antibody. For example, the PD-1 binding antagonist and/or PD-L1 binding antagonist can be selected from the group consisting of MDX-1106, Merck 3745, CT-011, AMP-224, AMP-514, YW243.55.S70, MPDL3280A, MDX-1105, MEDI-4736, and MSB0010718C.

In other embodiments, the subject is treated with at least one of tumor removal surgery, chemotherapy, radiation therapy, or immunotherapy.

In still other embodiments, the expression level of Cdk5 and/or PD-L1 in the cancer cells can be determined prior to administration of the Cdk5 inhibitor. The Cdk5 inhibitor can be administered to cancer cells where the PD-L1 expression level or Cdk5 expression level exceeds a predetermined threshold value. The predetermined threshold value can relate to cancer cell PD-L1 expression or Cdk5 expression.

Other embodiments described herein relate to a method of sensitizing cancer to immunotherapy or treating tumor immunity in a subject in need thereof. The method can include detecting the expression level of Cdk5 and/or programmed death-ligand 1 (PD-L1) in cancer cells. A subject having cancer cells expressing or over-expressing Cdk5 and/or PD-L1 can be administered an amount of a CdK5 inhibitor effective to suppress immune checkpoint PD-L1. The Cdk5 inhibitor can include, for example, at least one of Dinaciclib, AT7519, Roscovitine, CYCO65, PHA-793887, Milcidib, or SNS-032.

In other embodiments, the method can further include administering a PD-1 binding antagonist and/or a PD-L1 binding antagonist in combination with the Cdk5 inhibitor. The PD-1 binding antagonist and/or PD-L1 binding antagonist can inhibit PD-1/PD-L1 interaction and/or PD-1/PD-L1 signaling pathway.

In some embodiments, the PD-1 binding antagonist and/or PD-L1 binding antagonist is an antibody. For example, the PD-1 binding antagonist and/or PD-L1 binding antagonist can be selected from the group consisting of MDX-1106, Merck 3745, CT-011, AMP-224, AMP-514, YW243.55.S70, MPDL3280A, MDX-1105, MEDI-4736, and MSB0010718C.

In other embodiments, the subject is treated with at least one of tumor removal surgery, chemotherapy, radiation therapy, or immunotherapy.

In still other embodiments, the expression level of Cdk5 and/or PD-L1 in the cancer cells can be determined prior to administration of the Cdk5 inhibitor. The Cdk5 inhibitor can be administered to cancer cells where the PD-L1 expression level or Cdk5 expression level exceeds a predetermined threshold value. The predetermined threshold value can relate to cell surface PD-L1 expression or Cdk5 expression.

Still other embodiments relate to a method of treating cancers expressing or over-expressing programmed death-ligand 1 (PD-L1) and/or Cdk5 in a subject in need thereof. The method can include administering to the subject a therapeutically effective amount of a CdK5 inhibitor to suppress immune checkpoint PD-L1. Cancer cells that express or over express PD-L1 and/or Cdk5 can include, for example, medulloblastoma or rhabdomyosarcoma.

In some embodiments the Cdk5 inhibitor can be selected from the group consisting of Dinaciclib, AT7519, Roscovitine, CYCO65, PHA-793887, Milcidib, and SNS-032.

In other embodiments, the method can further include administering a PD-1 binding antagonist and/or a PD-L1 binding antagonist in combination with the Cdk5 inhibitor. The PD-1 binding antagonist and/or PD-L1 binding antagonist can inhibit PD-1/PD-L1 interaction and/or PD-1/PD-L1 signaling pathway.

In some embodiments, the PD-1 binding antagonist and/or PD-L1 binding antagonist is an antibody. For example, the PD-1 binding antagonist and/or PD-L1 binding antagonist can be selected from the group consisting of MDX-1106, Merck 3745, CT-011, AMP-224, AMP-514, YW243.55.S70, MPDL3280A, MDX-1105, MEDI-4736, and MSB0010718C.

In other embodiments, the subject is treated with at least one of tumor removal surgery, chemotherapy, radiation therapy, or immunotherapy.

In still other embodiments, the expression level of Cdk5 and/or PD-L1 in the cancer cells can be determined prior to administration of the Cdk5 inhibitor. The Cdk5 inhibitor can be administered to cancer cells where the PD-L1 expression level or Cdk5 expression level exceeds a predetermined threshold value. The predetermined threshold value can relate to cell surface PD-L1 expression or Cdk5 expression.

BRIEF DESCRIPTION OF THE DRAWINGS

FIGS. 1(A-E) illustrate immunoassays, images, and plots showing targeted deletion of Cdk5 in medulloblastoma (MB) results in rejection by CD4+ T cells. (A) Cdk5 and p35 proteins are expressed in murine and human MB cell lines in vitro. (B) MM1 shCdk5 and MM1 crCdk5 are deficient in Cdk5 protein expression. (C) TFS in C57BL/6J injected with MM1 crNeg or crCdk5 with various depleting antibodies (n=10/group). (D) IHC of clinical MB samples reveals an inverse correlation between tumor Cdk5 expression (top) and CD3+ T cell infiltration (bottom). Pearson correlation=−0.91. Scale bar=100 μm. (E) Tumor growth kinetics for individual animals in each group. Panel three is an inset of panel two. X indicates that an animal was euthanized due to tumor size or ulceration.

FIGS. 2(A-I) illustrate plots and graphs showing disruption of either Cdk5 gene expression or Cdk5 activity suppresses PD-L1 expression that cannot be overcome with IFNγ stimulation in both human and murine MB. (A) In vivo IFNγ mRNA expression in tumor extracts from i.c. inoculations (n=3 mice/group; +/−SD). (B) Cdk5 kinase activity in MM1 WT, shCdk5, and shNS over the course of 24-hour stimulation with IFNγ (black) and the addition of 10 μM Roscovitine (gray). EB: embryonic brain. (C) In vitro mRNA expression of PD-L1 by MM1 WT (white), crCdk5 (black), and crNeg (gray) with or without 24 hours of IFNγ stimulation. Values represent the average of 3 biological replicates+/−SD. (D) In vitro PD-L1 surface staining of MM1 WT (white), crCdk5 (black), crNeg (gray), and crPDL1 (striped) with or without 24 hours of IFNγ stimulation. Values represent the average MFI+/−SD compared to unstimulated MM1 WT over 7-8 replicates. (E) Fold change of surface PD-L1 expression in MM1 WT (circle), shCdk5 (square), and shNS (triangle) over the course of 48 hours. (F) MFI of PD-L1 and PD-L2 expressed in MM1 WT (white), shCdk5 (black), and shNS (gray). (G) PD-L1 mRNA expression in MM1 WT cells when treated with Roscovitine and stimulated with IFNγ for 24 hours. AU relative to untreated. (H) DAOY and UW228 human MB lines treated with Roscovitine and stimulated with IFNγ for 24 hours. MFI relative to untreated samples. (I) TFS of MM1 crNeg and crPDL1 over 36 days (n=10 mice/group). *P<0.05;  P<0.01; * P<0.001

FIGS. 3(A-C) illustrate immunoblots and graphs showing Cdk5 gene silencing alters the IFNγ signaling pathway and is associated with hyperphosphorylation of IRF2BP2. (A) IFNγ stimulation of MM1 WT, crCdk5, and crNeg for 24 hours. IFNγR downstream mediators STAT1, phosphorylated (p)STAT1, IRF1, IRF2, and IRF2BP2 were assayed. (B) In vitro mRNA analysis of IRF-1, IRF-2, and IRF2BP2 present in MM1 WT (white), crCdk5 (black), and crNeg (gray) after treatment with IFNγ for 24 hours. (C) Global phosphoproteomic analysis (left) of MM1 WT, crCdk5, and crNeg cells shows a change in phosphorylation status of 35 different phosphopeptides found in 18 of the 22 identified proteins (right). Twelve proteins exhibit only increased phosphorylation, three exhibit only decreased phosphorylation, and three have both increased and decreased phosphorylation sites.

FIGS. 4(A-H) illustrate images showing orthotopic Cdk5 deficient tumors exhibit PD-L1 staining, CD4+ Tumor infiltrating lymphocytes (TIL), and accumulating infiltrates of CD11b+ populations. (A) Tumors extracted 14 days post-inoculation from MM1 WT, shCdk5, or shNS stained for PD-L1 expression. Right panel (Scale bar=400 μm) is an inset of the boxed region on the left (Scale bars=2 mm). (B), (C) FACS analysis of MM1 WT (black circle) and MM1 crCdk5 (red square) tumor infiltrate by percentage of cell type. (D) Ratio of total CD8+:CD4+ cell infiltrate. (E) FACS analysis of the percentage of PD-1+ or PD-L1+ cells in the CD4+ or CD8+ populations. (F) FACS analysis of the percentage of myeloid cells in tumor infiltrate based on differential CD45 staining (left) or Ly6C staining among CD11b+CD45+ cells (right). (G) Percent of total CD11b+ population (left) and sub-populations (right) present in tumor infiltrate that express PD-L1. (H) MFI of PD-L1 expression among CD11b+ total population (left) and sub-populations (right). (B), (C), (D), (E), (F) and (G) were graphed as the mean+/−SD. (H) was graphed as individual MFI with mean indicated. n=9/group. Each data point represents pooled samples from 3 mice. *$P<0.05$; **$P<0.01$ FIGS. 5(A-E) illustrate plots and graphs showing kinase active Cdk5 is expressed by murine and human MB cell lines and deletion of Cdk5 does not alter proliferation. (A) Genomic analysis from the UCSC cancer genome browser demonstrates that Cdk5, p35, and p39 are highly expressed in pediatric MB and neuroblastoma (NB) samples (above black line) compared to normal brain tissue (below black line). (B) Cdk5 kinase assay activity is detected in human MB (UW228, DAOY) and mouse MB (MM1) cell lines, with lysates from $Cdk5^{-/-}$ and Cdk5+/+ embryonic brains as negative and positive controls, respectively (Black Bars). The non-selective Cdk5 inhibitor, Roscovitine (10 μM), abrogates this kinase activity (Gray bars). (C) mRNA expression of Cdk5 transcript in MM1 WT (white), shCdk5 (black), or shNS (gray). (D) Proliferation curves of MM1 WT (square), shCdk5 (triangle), and shNS (circle) in media with 10% serum (black lines) or 1% serum (gray lines) over 72 hours (E) Proliferation curves of MM1 WT (white), crCdk5 (black), crNeg (gray) in media containing 10% serum over 72 hours.

FIGS. 6(A-D) illustrate plots showing similar subcutaneous growth kinetics of crCdk5 MM1 and crNeg MM1 in immunecompromised mice. (A) In vivo, growth kinetics of MM1 crCdk5 (circle) and crNeg (square) in NSG mice (n=10/group). Points were graphed as the average size+/−SD. (B) TFS of MM1 crCdk5 (circle) and crNeg (square) in NSG mice. (C) Tumor weights of MM1 crCdk5 (circle) and crNeg (square) in NSG mice. The solid line represents the average weight+/−SD. (D) Inverse correlation between CD3+ cell count per HPF and Cdk5 staining intensity of clinical MB tissue samples as revealed by IHC analysis in FIG. 1D.

FIGS. 7(A-E) illustrate plots showing in vivo growth kinetics of MM1 shCdk5 reveals thymic dependent tumor rejection upon subcutaneous (S.C.) injection. (A) TFS of MM1 WT (diamond, n=13), shCdk5 (circle, n=17), and shNS in B6 mice (triangle, n=7). Survival curves were calculated from 3 independent experiments. (B) Tumor weights of MM1 WT (triangles, n=13) and shCdk5 (circles, n=13) and shNS (squares, n=7). The solid line represents the average weight+/−SD. (C) TFS of B6 mice injected s.c. with MM1 shNS (diamond, n=10) or MM1 shCdk5 (circle) with injection of αCD4 (triangle), αCD8 (inverted triangle), or αCD4 and αCD8 (square) antibodies (n=15/group). (D) Tumor size measurement of MHC-II KO (circle) and MHC-I KO (square) mice injected s.c. with Cdk5-deficient MM1 (n=10/group). (E) TFS of B6 mice re-challenged with MM1 WT at least 60 days post-initial injection of MM1 shCdk5 (square) or MM1 crCdk5 (circle) (n=5/group). $P<0.01$; *$P<0.001$ FIGS. 8(A-E) illustrate plots showing a link between Cdk5 and PD-L1 expressions in human and murine tumors. (A) Cdk5 expression of cells cultured from subcutaneous tumor outgrowths isolated from animals initially injected with MM1 WT (n=4), crCdk5 (n=4), or crNeg (n=6). (B) PD-L1 expression on primary cell cultures of MM1 crNeg, crCdk5, or outgrowth of crCdk5 tumors. Cells were stimulated with IFNγ for 24 hours (black) and compared to isotype staining (dotted line) and unstimulated cells (gray). Histogram is a representative staining from three separate experiments. (C) PD-L1 mRNA expression by RMS 76.9 WT (white), shCdk5 (black), and shNS (gray) with or without 24 hours of IFNγ stimulation. (D) Surface PD-L1 staining of RMS 76.9 shNS (gray) and shCdk5 (black) with or without 24 hours of IFNγ stimulation. Values represent the average MFI+/−SD compared to unstimulated RMS 76.9 shNS over three independent experiments. (E) Surface PD-L1 staining of SJCRH30 WT (white) and crCdk5 (black) with or without 24 hours of IFNγ stimulation in vitro. Values represent average MFI+/−SD compared to unstimulated WT over three independent experiments. *, $P<0.05$; **, $P<0.005$.

FIGS. 9(A-B) illustrate plots showing co-occurrence of upregulated Cdk5 and PD-L1 expression in human cancer samples. TCGA provisional datasets for all available cancer types were analyzed for Cdk5 and PD-L1 (CD274) mRNA expression through cBioPortal (http://www.cbioportal.org/). (A) Variable levels of Cdk5 and PD-L1 gene expression are detected in all cancer subtypes. Relative mRNA expression values of samples with existing RNA sequencing analysis (RNA Seq V2) were downloaded and analyzed with Microsoft excel. The average log 2 mRNA expression across each cancer type examined was individually graphed for Cdk5 and PD-L1. (B) Co-occurrence of elevated Cdk5 and PD-L1 gene expression is observed in several cancer types. Cancer samples with available mRNA expression data were analyzed for co-occurrence or mutual exclusivity of Cdk5 and PD-L1 overexpression. mRNA expression z-scores of RNA Seq V2 RSEM from available tumors were analyzed for significance, their log odds ratio, and type of association. Representative cancer types showing co-occurrence of elevated Cdk5 and PD-L1 transcript levels are displayed.

FIGS. 10(A-C) illustrate plots and an immunoassay showing silencing Cdk5 in MB alters IRF-2 expression but does not affect other IFN signaling pathways. (A) Surface expression of MHC-I is upregulated on MM1 WT, crCdk5, and crNeg. Cells were stimulated with IFNγ for 24 hours (black)

Figure 18C:
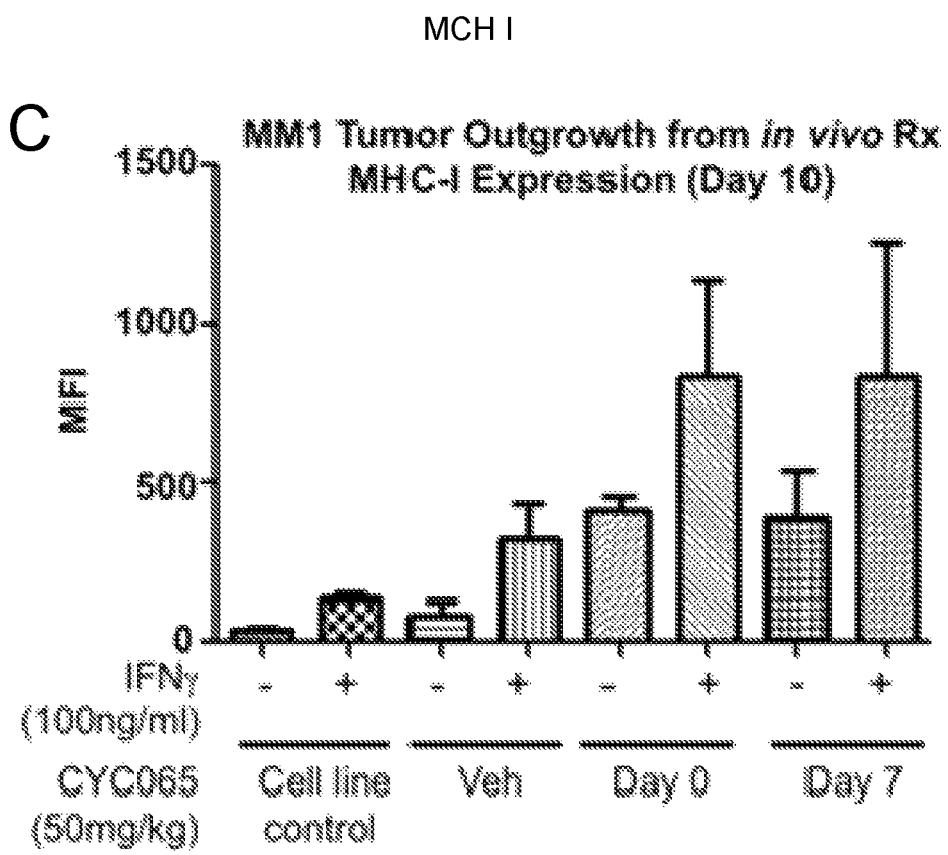

and compared to isotype staining (dotted line) and unstimulated cells (gray). Histogram is a representative staining from three separate experiments. (B) IFNγ stimulation of MM1 WT, crCdk5, and crNeg over the course of 48 hours. IFNγR downstream mediators IRF1, and IRF2 were assayed. (C) 24-hour stimulation of MM1 WT, crCdk5, and crNeg cells. Downstream IFNγ pathway elements STAT5, phosphorylated (p)STAT3, and STAT2 were assayed.

FIGS. 11(A-D) illustrate an immunoassay, images, and plots showing CD3+ cell infiltrate and diminished growth rates associate with a decrease in tumor incidence following orthotopic administration of Cdk5-deficient MM1 cells. (A) Tumor incidence of MM1 WT, shCdk5, and shNS 14 days after i.c. tumor inoculation. (B) Western blot analysis for Cdk5 in cells cultured from B6 mice tumor outgrowths initially inoculated with MM1 WT (n=2) and MM1 crCdk5 (n=3). (C) IHC of tumor injected i.c. with MM1 WT, shCdk5, and shNS (scale bar=200 μm). (D) Quantification of intratumoral CD3+ cells in MM1 WT (n=3), shCdk5 (n=3), and shNS (n=4) tumors identified via IHC per mm2 of tumor tissue. Solid line represents the average+/−SD.

FIGS. 12(A-I) illustrate graphs, images, and plots showing subcutaneous Cdk5 deficient tumors characterized by increased stromal PD-L1 staining, CD4+ tumor infiltrating lymphocytes (TIL), and infiltrating CD11b+ populations. (A) In vivo IFNγ mRNA expression in tumor extracts from subcutaneous inoculations (n=3 mice/group; +/−SD). (B) Subcutaneous Tumors extracted 14 days post-inoculation from MM1 shCdk5 or shNS stained for F4/80, PD-L1, and PD-1 expression (Scale bars=2 mm). (C), (D) FACS analysis of MM1 WT (black circle) and MM1 crCdk5 (red square) tumor infiltrate by percentage of cell type. (E) Ratio of total CD8+:CD4+ cell infiltrate. (F) FACS analysis of the percentage of PD-1+ or PD-L1+ cells in the CD4+ or CD8+ populations. (G) FACS analysis of the percentage of myeloid cells in tumor infiltrate based on differential CD45 staining (left) or Ly6C staining among CD11b+CD45+ cells (right). (H) Percent of total CD11b+ population (left) and sub-populations (right) present in tumor infiltrate that express PD-L1. (I) MFI of PD-L1 expression between total (left) and sub-populations (right) of CD11b+ cells. C thru H were graphed as the mean+/−SD. (I) was graphed as individual MFI with mean indicated. n=9/group. Each data point represents pooled samples from 3 mice. *P<0.05

FIGS. 13(A-B) illustrate schema of putative mechanism by which Cdk5 controls PD-L1 expression. (A) When Cdk5 WT cells are stimulated with IFNγ, signaling through the JAK/STAT pathway stimulates IRF-1 driven transcription of PD-L1. Additionally, IFNγ stimulates p35 expression and thereby increases Cdk5 activity. Phosphorylation of unknown kinase(s) by Cdk5 inhibits kinase function, resulting in a reduced abundance of the IRF2/IRF2BP2 repressor complex. (B) In Cdk5 deficient cells, unknown kinase(s) hyper-phosphorylate IRF2BP2, prolong half-life of IRF2/IRF2BP2 repressor complex despite intact JAK/STAT/IRF-1 signaling, ultimately leading to decreased PD-L1 expression. IRF-E: IRF-binding element.

FIGS. 14(A-F) illustrate plots showing higher Cdk5 correlates with adverse clinical outcomes in human cancers. PrognoScan database-based Kaplan-Meier analysis of six independent patient cohorts including CNS and peripheral tumors that were analyzed for the effects of higher levels of Cdk5 gene expression (red) compared to low Cdk5 levels (blue) on overall survival, disease free survival, or metastasis free survival (http://www.prognoscan.org/). High levels of Cdk5 are associated with reduced (A) overall survival in a cohort of 74 glioma patients with astrocytoma (n=8), GBM (n=50), mixed glioma (n=7), and oligodendroglioma (n=9) (GSE 4412-GPL96); (B) overall survival in 50 patients with anaplastic oligodendroglioma (n=22) and GBM (n=28) (MGHglioma); (C) overall survival of cutaneous melanoma patients (n=38) (GSE19234); (D) distant metastasis free survival in uveal melanoma patients (n=63) (GSE22138); (E) overall survival in a cohort of 104 patients with lung adenocarcinoma (GSE68465); and (F) disease free survival in a cohort of 249 breast cancer patients (GSE4922-GPL96). All p-values represent the corrected p-value.

FIGS. 15(A-B) illustrate graphs showing surface PD-L1 expression on MM1 cells following 24-hour exposure of IFNγ (100 ng/ml) and various concentrations of CYC065. (A) Mean fluorescence intensity as measured by flow cytometry. (B) Fold change in PD-L1 MFI before and after IFNγ exposure. Fold change=$(MFI_{+IFN\gamma}-MFI_{-IFN\gamma}/MFI_{-IFN\gamma})$.

FIGS. 16(A-B) illustrate graphs showing surface PD-L1 expression on RMS 76.9 cells following 24-hour exposure of IFNγ (100 ng/ml) and various concentrations of CYC065. (A) Mean fluorescence intensity as measured by flow cytometry. (B) Fold change in PD-L1 MFI before and after IFNγ exposure. Fold change=$(MFI_{+IFN\gamma}-MFI_{-IFN\gamma}/MFI_{-IFN\gamma})$.

FIGS. 17(A-C) illustrate plots showing tumor incidence (A), overall mortality (B) and tumor size (C) of MM1-bearing C57BL/6 mice treated with 50 mg/kg daily×5 days/week dose of CYC065 in water by gavage. CYC065 was started either beginning on Day 0 (red line) or Day 7 (green line) following tumor inoculation. There is a 70% mortality associated with prolonged exposure of mice to CYC065. However, mice treated with CYC065 developed significantly smaller sized tumor.

FIGS. 18(A-C) illustrate graphs showing tumor cells harvested on Day 21 of tumor-bearing mice treated in FIG. 17 were cultured in vitro for 7-10 days, and then subjected to stimulation with 100 ng/ml of IFNγ for 24 hours. The surface expressions of PD-L1 (A), MHC Class II molecule, I-$A^b$ (B) and MHC Class I molecules, $K^bD^b$ (C) were analyzed by flow cytometry.

DETAILED DESCRIPTION

For convenience, certain terms employed in the specification, examples, and appended claims are collected here. Unless defined otherwise, all technical and scientific terms used herein have the same meaning as commonly understood by one of ordinary skill in the art to which this invention belongs.

A "cancer" refers a broad group of various diseases characterized by the uncontrolled growth of abnormal cells in the body. Unregulated cell division and growth divide and grow results in the formation of malignant tumors that invade neighboring tissues and may also metastasize to distant parts of the body through the lymphatic system or bloodstream.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

An "immunoregulator" refers to a substance, an agent, a signaling pathway or a component thereof that regulates an immune response. "Regulating," "modifying" or "modulating" an immune response refers to any alteration in a cell of the immune system or in the activity of such cell. Such regulation includes stimulation or suppression of the immune system which may be manifested by an increase or decrease in the number of various cell types, an increase or decrease in the activity of these cells, or any other changes which can occur within the immune system. Both inhibitory and stimulatory immunoregulators have been identified, some of which may have enhanced function in the cancer microenvironment.

The term "immunotherapy" refers to the treatment of a subject afflicted with, or at risk of contracting or suffering a recurrence of, a disease by a method comprising inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication, condition or biochemical indicia associated with a disease.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

The "Programmed Death-1 (PD-1)" receptor refers to an immunoinhibitory receptor belonging to the CD28 family PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GENBANK Accession No. U64863.

"Programmed Death Ligand-1 (PD-L1)" is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GENBANK Accession No. Q9NZQ7.

A "signal transduction pathway" or "signaling pathway" refers to the biochemical relationship between a variety of signal transduction molecules that play a role in the transmission of a signal from one portion of a cell to another portion of the cell. A "cell surface receptor" includes, for example, molecules and complexes of molecules that are located on the surface of a cell and are capable of receiving a signal and transmitting such a signal across the plasma membrane of a cell. An example of a cell surface receptor of the present invention is the PD-1 receptor, which is located on the surface of activated B cells, activated T cells and myeloid cells, and transmits a signal that results in a decrease in tumor-infiltrating lymphocytes and a decrease in T cell proliferation. An "inhibitor" of signaling refers to a compound or agent that antagonizes or reduces the initiation, reception or transmission of a signal, be that signal stimulatory or inhibitory, by any component of a signaling pathway such as a receptor or its ligand.

A "subject" includes any human or nonhuman animal. The term "nonhuman animal" includes, but is not limited to, vertebrates such as nonhuman primates, sheep, dogs, cats, rabbits, ferrets, rodents such as mice, rats and guinea pigs, avian species such as chickens, amphibians, and reptiles. In preferred embodiments, the subject is a mammal such as a nonhuman primate, sheep, dog, cat, rabbit, ferret or rodent. In more preferred embodiments, the subject is a human. The terms, "subject," "patient" and "individual" are used interchangeably herein.

A "therapeutically effective amount" or "therapeutically effective dosage" of a drug or therapeutic agent, such as an Ab of the invention, is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of the drug preferably inhibits cell growth or tumor growth by at least about 20%, more preferably by at least about 40%, even more preferably by at least about 60%, and still more preferably by at least about 80% relative to untreated subjects. In other preferred embodiments of the invention, tumor regression may be observed and continue for a period of at least about 20 days, more preferably at least about 40 days, or even more preferably at least about 60 days. Notwithstanding these ultimate measurements of therapeutic effectiveness, evaluation of immunotherapeutic drugs must also make allowance for "immune-related" response patterns.

An "immune-related" response pattern refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents may require long-term monitoring of the effects of these agents on the target disease.

A therapeutically effective amount of a drug includes a "prophylactically effective amount," which is any amount of the drug that, when administered alone or in combination with an anti-neoplastic agent to a subject at risk of developing a cancer (e.g., a subject having a pre-malignant condition) or of suffering a recurrence of cancer, inhibits the development or recurrence of the cancer. In preferred embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

A "tumor-infiltrating inflammatory cell" is any type of cell that typically participates in an inflammatory response in a subject and which infiltrates tumor tissue. Such cells include tumor-infiltrating lymphocytes (TILs), macrophages, monocytes, eosinophils, histiocytes and dendritic cells.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Treatment" refers to clinical intervention designed to alter the natural course of the individual or cell being treated, and can be performed either for prophylaxis or during the course of clinical pathology. Desirable effects of treatment include preventing occurrence or recurrence of disease, preventing metastasis, decreasing the rate of disease progression, ameliorating or palliating the disease state, and remission or improved prognosis.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile.

The term "about" as used herein refers to the usual error range for the respective value readily known to the skilled person in this technical field.

The use of the alternative (e.g., "or") should be understood to mean either one, both, or any combination thereof of the alternatives. As used herein, the indefinite articles "a" or "an" should be understood to refer to "one or more" of any recited or enumerated component.

Embodiments described herein relate to a method of sensitizing cancer to immunotherapy, treating tumor immunity, and/or treating cancers expressing or over-expressing programmed cell death ligand 1 (PD-L1) and/or Cdk5 in a subject in need thereof by administering to the subject a therapeutically effective amount of a CdK5 inhibitor to suppress immune checkpoint programmed death-ligand 1 (PD-L1) in the cancer cells and promote T-cell mediated tumor immunity.

Cancers often evade immune surveillance by adopting peripheral tissue-tolerance mechanisms, such as the expression of programmed cell death ligand 1 (PD-L1). It was found that cyclin-dependent kinase 5 (Cdk5), a serine-threonine kinase that is highly active in postmitotic neurons and in many cancers, can allow PD-L1 expressing or over-expressing cancers to evade immune elimination. PD-L1 up-regulation can be induced in some cancer cells by Interferon-γ (IFN-γ). Induction of PD-L1 by IFN-γ requires Cdk5. Loss or inhibition of Cdk5 results in persistent expression of the PD-L1 transcriptional repressors, the interferon regulatory factors IRF2 and IRF2BP2, which leads to reduced PD-L1 expression on tumors. Accordingly, disruption of Cdk5 activity in the cancer cells with a Cdk5 inhibitor results in potent T cell-mediated tumor rejection. Moreover, this effect is mediated via posttranslational modification of IRF2BP2, leading to the increased abundance of IRF2/IRF2BP2 and sustained functional repression of PD-L1 transcription following IFNγ stimulation.

In some embodiments, cancer cells of the subject treated with the Cdk5 inhibitor can express or overexpress PD-L1 and/or Cdk5. Examples of cancer cells that can potentially express or overexpress PD-L1 and/or Cdk5 can include liver cancer, bone cancer, pancreatic cancer, skin cancer, cancer of the head or neck, breast cancer, lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, precursor T-lymphoblastic lymphoma, metastatic cancers and any combinations of said cancers.

In other embodiments, a cancer that expresses or overexpresses PD-L1 and/or Cdk5 can include glioblastoma multiforme, adrenocortical carcinoma, hepatocellular carcinoma, pheochomocytoma/paraganglioma, cutaneous melanoma, uveal melanoma, uterine carcinosarcoma, diffuse large b-cell lymphoma, low grade glioma, testicular germ cell tumor, papillary renal cell carcinoma, endometrial carcinoma, mesothelioma, thymoma, ovarian high-grade serous carcinoma, bladder urothelial carcinoma, colorectal adenocarcinoma, cholangiocarcinoma, sarcoma, lung squamous cell carcinoma, cervical squamous cell carcinoma, prostatic adenocarcinoma, lung adenocarcinoma, chomophobe renal cell carcinoma, pancreatic adenocarcinoma, head and neck squamous cell carcinoma, clear cell renal cell carcinoma, thryroid carcinoma, acute myeloid leukemia, rhabdomyosarcoma, and breast invasive cell carcinoma.

In still other embodiments, a cancer that expresses or overexpresses PD-L1 and/or Cdk5 can include medulloblastoma or rhabdomyosarcoma.

The Cdk5 inhibitor administered to the subject to sensitize the cancer to immunotherapy, treat tumor immunity, and/or treat cancers expressing or over-expressing programmed cell death ligand 1 (PD-L1) and/or Cdk5 can include any therapeutic agent that inhibits or reduces one or more of, the catalytic activity and function of the Cdk5 to suppress immune checkpoint programmed death-ligand 1 (PD-L1) in the cancer cells and/or promote persistent expression of the PD-L1 transcriptional repressors, the interferon regulatory factors IRF2 and IRF2BP2, which likely leads to reduced PD-L1 expression on tumors. The catalytic or functional activity of the Cdk5 can be suppressed, inhibited, and/or blocked in several ways including: direct inhibition of the activity of Cdk5 (e.g., by using neutralizing antibodies, small molecules or peptidomimetics, dominant negative polypeptides); inhibition of genes that express the Cdk5 (e.g., by blocking the expression or activity of the genes and/or proteins); activation of genes and/or proteins that inhibit one or more of, the catalytic activity and function of Cdk5 (e.g., by increasing the expression or activity of the genes and/or proteins); inhibition of genes and/or proteins that are downstream mediators of the Cdk5 (e.g., by blocking the expression and/or activity of the mediator genes and/or proteins); introduction of genes and/or proteins that negatively regulate one or more of, catalytic activity and function of Cdk5 (e.g., by using recombinant gene expression vectors, recombinant viral vectors or recombinant polypeptides); or gene replacement with, for instance, a hypomorphic mutant of Cdk % (e.g., by homologous recombination, overexpression using recombinant gene expression or viral vectors, or mutagenesis).

In some embodiments, the Cdk5 inhibitor can be a selective or non-selective CdK5 inhibitor. Examples of selective and non-selective Cdk5 inhibitors include Dinaciclib, AT7519, Roscovitine, CYC065, PHA-793887, PHA-767491, Milcidib, and SNS-032. Other examples of Cdk5 inhibitors include purvalanol A, purvalanol B, olomucine, and 2,6,9-trisubstituted purines as described in WO97/20842, WO98/05335, WO99/07705, US 2009/0325983, and US 2010/0093769, which are all incorporate by reference in their entirety.

In a particular embodiment, the Cdk5 inhibitor can include roscovitine or CYC069, which are 2,6,9-trisubstituted purines that are commercially available from Cyclacel Limited.

Although the Cdk5 inhibitors described herein (including their pharmaceutically acceptable salts, esters and pharmaceutically acceptable solvates) can be administered alone, for human therapy they will generally be administered in admixture with a pharmaceutical carrier, excipient or diluent.

Other embodiments described herein therefore relate to a pharmaceutical composition comprising a Cdk5 inhibitor admixed with a pharmaceutically acceptable excipient, diluent or carrier. Examples of such excipients for the various different forms of pharmaceutical compositions described herein may be found in the "Handbook of Pharmaceutical Excipients, 2nd Edition, (1994), Edited by A Wade and P J Weller.

Carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

The Cdk5 inhibitors described herein can be present as salts or esters, in particular pharmaceutically acceptable salts or esters.

Pharmaceutically acceptable salts of the Cdk5 inhibitors described herein include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g., sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as (C1-C4)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as (C1-C4)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g., by a halogen).

Pharmaceutical compositions including Cdk5 inhibitors described herein may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from about 1 mg to about 2000 mg and, more preferably, from about 25 mg to about 1000 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredients can be incorporated into a cream consisting of an aqueous emulsion of polyethylene glycols or liquid paraffin. The active ingredients can also be incorporated, at a concentration of between 1 and 10% by weight, into an ointment consisting of a white wax or white soft paraffin base together with such stabilisers and preservatives as may be required.

Injectable forms may contain between about 10 mg to about 1000 mg, preferably between about 10 to about 500 mg, of active ingredient per dose.

Compositions may be formulated in unit dosage form, i.e., in the form of discrete portions containing a unit dose, or a multiple or sub-unit of a unit dose.

In a particularly preferred embodiment, the combination or pharmaceutical composition of the invention is administered intravenously.

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific agents employed, the metabolic stability and length of action of that agent, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the Cdk5 inhibitor may be administered at a dose of from 0.1 to 100 mg/kg body weight, or from 2 to 50 mg/kg, more preferably from 0.1 to 25 mg/kg body weight.

In some embodiments, a Cdk5 inhibitor, such as roscovitine or CYC065, can be administered orally or intravenously at a dosage of from about 0.05 to about 5 g/day, preferably from about 0.5 to about 5 g/day or 1 to about 5 g/day, and even more preferably from about 1 to about 3 g/day. Alternatively, the Cdk5 inhibitor can be administered at a dosage of about 0.4 to about 3 g/day. Roscovitine and CYC065 can be administered orally in tablets or capsules. The total daily dose of the Cdk5 inhibitor can be administered as a single dose or divided into separate dosages administered two, three or four time a day.

In other embodiments, the method can further include administering PD-L1/PD-1 signaling pathway inhibitor, PD-1 binding antagonist, and/or a PD-L1 binding antagonist in combination with the Cdk5 inhibitor. The PD-L1/PD-1 signaling pathway inhibitor, PD-1 binding antagonist and/or PD-L1 binding antagonist can inhibit PD-1/PD-L1 interaction and/or PD-1/PD-L1 signaling pathway.

Emerging clinical data support the critical role of PD-L1/PD-1 signaling in tumor immune evasion, with roughly 30% of tumors responding to immune checkpoint blockade Immunotherapy approaches targeting the PD-L1/PD-1 pathway have achieved a durable rejection of central nervous system (CNS) malignancies in preclinical models. Furthermore, high Cdk5 gene expression is associated with either decreased overall survival or decreased disease free or metastasis free survival in cutaneous melanoma, glioma, breast and lung cancer (FIG. 14), and clinical trials with anti-PD-1/anti-PD-L1 therapy in patients with these cancers are underway.

The PD-L1/PD-1 signaling pathway inhibitor can include any molecule that inhibits the interaction of a PD-L1/PD-1 binding partner with either one or more of its binding partner, so as to remove T-cell dysfunction resulting from signaling on the PD-L1/PD-1 signaling with a result being to restore or enhance T-cell function (e.g., proliferation, cytokine production, target cell killing). As used herein, a PD-L/PD-1 signaling pathway inhibitor includes a PD-1 binding antagonist and a PD-L1 binding antagonist.

The PD-1 binding antagonist can include a molecule that decreases, blocks, inhibits, abrogates or interferes with signal transduction resulting from the interaction of PD-1 with one or more of its binding partners, such as PD-L1 or PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1 106 described herein. In another specific aspect, a PD-1 binding antagonist is Merck 3745 described herein. In another specific aspect, a PD-1 binding antagonist is CT-01 1 described herein.

In some embodiments, the anti-PD-1 antibody is MK-3475 (formerly lambrolizumab, Merck), AMP-514, AMP-224 (MedImmune/AstraZeneca), BMS-936558 (MDX-1106, Bristol-Myers Squibb), or CT-011 (Curetech).

Pembrolizumab (MK-3475) is a humanized, monoclonal anti-PD-1 antibody designed to reactivate anti-tumor immunity. Pembrolizumab exerts dual ligand blockade of the PD-1 pathway by inhibiting the interaction of PD-1 on T cells with its ligands PD-L1 and PD-L2.

In some embodiments, the anti-PD-1 antibody is one of the antibodies disclosed in U.S. Pat. Nos. 8,354,509, and 8,168,757, the disclosure of which is incorporated by reference in their entirety.

Nivolumab (also known as BMS-936558 or MDX1106, is a fully human IgG4 monoclonal antibody developed by Bristol-Myers Squibb for the treatment of cancer.

In some embodiments, the anti-PD-1 antibody is one of the antibodies disclosed in WO2004/056875, U.S. Pat. Nos. 7,488,802 and 8,008,449, the disclosure of which is incorporated by reference in their entirety.

AMP-514 and AMP-224 are an anti-programmed cell death 1 (PD-1) monoclonal antibody (mAb) developed by Amplimmune, which was acquired by MedImmune.

In some embodiments, the anti-PD-1 antibody is one of the antibodies disclosed in US Appl. Pub. No. 20140044738, the disclosure of which is incorporated by reference in their entirety.

Pidilizumab (CT-011) is an anti-PD-1 monoclonal antibody developed by Israel-based Curetech Ltd.

In some embodiments, the anti-PD-1 antibody is one of the antibodies disclosed in US Pat. Appl. Pub. Nos. 20080025980 and 20130022595, the disclosure of which is incorporated by reference in their entirety.

The PD-L 1 binding antagonist can include any molecule that decreases, blocks, inhibits, abrogates or interferes with signal transduction resulting from the interaction of PD-L1 with either one or more of its binding partners, such as PD-1. In some embodiments, a PD-L1 binding antagonist is a molecule that inhibits the binding of PD-L 1 to its binding partners. In a specific aspect, the PD-L1 binding antagonist inhibits binding of PD-L 1 to PD-1. In some embodiments, the PD-L 1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L 1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L 1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is MPDL3280A described herein.

In some embodiments, the anti-PD-L1 antibody is MPDL3280A and YW243.55.S70, (Genentech/Roche), MEDI-4736 (MedImmune/AstraZeneca), BMS-936559 (MDX-1105, Bristol-Myers Squibb), and MSB0010718C (EMD Serono/Merck KGaA). MPDL3280A (Genentech) is an engineered anti-PD-L1 antibody designed to target PD-L1 expressed on tumor cells and tumor-infiltrating immune cells. MPDL3280A is designed to prevent PD-L1 from binding to PD-1 and B7.1. This blockade of PD-L1 may enable the activation of T cells, restoring their ability to detect and attack tumor cells. MPDL3280A contains an engineered fragment crystallizable (Fc) domain designed to optimize efficacy and safety by minimizing antibody-dependent cellular cytotoxicity (ADCC).

In some embodiments, the anti-PD-L1 antibody is one of the antibodies disclosed in U.S. Pat. No. 7,943,743, the disclosure of which is incorporated by reference in their entirety.

BMS-936559 (MDX-1105, Bristol-Myers Squibb) is a fully human IgG4 anti-PD-L1 mAb that inhibits the binding of the PD-L1 ligand to both PD-1 and CD80.

In some embodiments, the anti-PD-L1 antibody is one of the antibodies disclosed in U.S. Pat. No. 7,943,743, the disclosure of which is incorporated by reference in their entirety.

MSB0010718C (EMD Serono of Merck KGaA) is fully human IgG1 monoclonal antibody that binds to PD-L1.

In some embodiments, the anti-PD-L1 antibody is one of the antibodies disclosed in WO 2013079174 A1, the disclosure of which is incorporated by reference in their entirety.

MEDI4736 (MedImmune/AstraZeneca) is a human IgG1 antibody which binds specifically to PD-L1, preventing binding to PD-1 and CD80.

In some embodiments, the anti-PD-L1 antibody is one of the antibodies disclosed in WO 2011066389 A1 and U.S. Pat. No. 8,779,108, the disclosure of which is incorporated by reference in their entirety.

In some embodiments, the anti-PD-L1 antibody is one of the antibodies disclosed in U.S. Pat. No. 8,552,154, the disclosure of which is incorporated by reference in their entirety Disruption of the PD-1/PD-L1 interaction by antagonistic Abs can enhance the immune response to cancerous cells in a patient. PD-L1 is not expressed in normal human cells, but is abundant in a variety of human cancers (Dong et al., 2002). The interaction between PD-1 and PD-L1 impairs T cell responses as manifested by a decrease in tumor-infiltrating lymphocytes (TILs) and a decrease in T-cell receptor mediated proliferation, resulting in T cell anergy, exhaustion or apoptosis, and immune evasion by the cancerous cells Immune suppression can be reversed by inhibiting the local interaction between PD-L1 and PD-1 using an anti-PD-1 and/or an anti-PD-L1 Ab. These Abs may be used alone or in combination with the Cdk5 inhibitors described herein to inhibit the growth of cancerous tumors.

It will be appreciated that Cdk5 inhibitors and optionally a PD-L1/PD-1 signaling pathway inhibitor can be administered to a subject that has or is to be treated with at least one of a immunotherapy, tumor removal surgery, chemotherapy, and/or radiation therapy.

Immunotherapeutics, which can be administered in combination with the Cdk5 inhibitors described herein and optionally the PD-L1/PD-1 signaling pathway inhibitor, can directly or indirectly, affect toll like receptors, nucleotide-oligomerization domain-like receptors, RIG-I-Like receptors, c-type lectin receptors, or cytosolic DNA Sensors, or a combination thereof. Particularly, the immunotherapeutics are capable of activating a human plasmacytoid dendritic cell, myeloid dendritic cell, NK cell, or tumor cell, or a combination thereof.

In some embodiments, the immunotherapeutics activate human immune cells, including but not limited to dendritic cells, macrophages, monocytes, myeloid-derived suppressor cells, NK cells, B cells, T cells, or tumor cells, or a combination thereof.

In other embodiments, the immunotherapeutic can include an immune cell that is administered to the subject. The immune cell can be a dendritic cell, engineered dendritic cell, T-cell, or engineered T-cell, or a combination thereof. In some embodiments, the immune cell is isolated from the subject.

In various embodiments, the dendritic cells are autologous dendritic cells or allogeneic dendritic cells. In various embodiments, dendritic cells suitable for use in accordance with the present invention are isolated or obtained from any tissue in which such cells are found, or are otherwise cultured and provided. Dendritic cells may be found, for example, but in no way limited to, in the bone marrow, in peripheral blood mononuclear cells (PBMCs) of a mammal or in the spleen of a mammal. Additionally, any suitable media that promote the growth of dendritic cells may be used in accordance with the present invention, and may be readily ascertained by one skilled in the art.

In various embodiments, the immune cell is primed against a tumor cell lysate, tumor cell antigen, tumor cell cytokine, and/or stem cell lysate. In some embodiments, the tumor cell lysate comprises lysate prepared or derived from the nervous system tumor in the subject who has been, is being, or will be treated by a method described herein. In other embodiments, the tumor cell lysate comprises lysate prepared or derived from a nervous system tumor in another subject.

In various embodiments, the tumor cell lysate, tumor cell antigen, or tumor cell cytokine is prepared from a system tumor. In various embodiments, the tumor cell lysate, tumor cell antigen, tumor cell cytokine, and/or stem cell lysate is prepared from a biological sample. In one embodiment, the biological sample comprises tumor cells, cancerous cells, cells from a tumor, tumor tissue, cancerous tissue, and/or a tumor biopsy. In one embodiment, the biological sample is obtained from the subject who has been, is being, or will be treated by a method described herein. In another embodiment, the biological sample is obtained from another subject.

In various embodiments, the immune cell is administered to the subject intravenously. In accordance with the invention, the ventricle can be any ventricle in the nervous system. Typical dosages of an effective amount of the immune cell can be as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models.

In various embodiments, the immune cell is administered once a day (SID/QD), twice a day (BID), three times a day (TID), four times a day (QID), or more, so as to administer an effective amount of the immune cell to the subject, where the effective amount is any one or more of the doses described herein.

In some embodiments, the immune cell is administered at the prevention stage of a tumor (i.e., when the subject has not developed the tumor but is likely to or in the process to develop the tumor). In other embodiments, the immune cell is administered at the treatment stage of a tumor (i.e., when the subject has already developed the tumor).

The chemotherapeutic agent administered in combination with the Cdk5 inhibitor and optionally the PD-L1/PD-1 signaling pathway inhibitor is a chemical compound useful in the treatment of cancer. Examples of chemotherapeutic agents include alkylating agents such as thiotepa and cyclophosphamide; alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and butlatacinone); delta-9-tetrahydrocannabinol (dronabinol); beta-lapachone; lapachol; colchicines, betulinic acid; a camptothecin (including the synthetic analogue topotecan (CPT-11 (irinotecan), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocamicin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholphosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Nicolaou et ah, Angew. Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, doxorubicin HC1 liposome injection and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine, tegafur, capecitabine, an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-Kit inhibitors; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK.RTM. polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); thiotepa; taxoids, e.g., paclitaxel, albumin-engineered nanoparticle formulation of paclitaxel, and doxetaxel; chloranbucil; 6-thioguanine; mercaptopurine; methotrexate; platinum analogs such as cisplatin and carboplatin; vinblastine; platinum; etoposide (VP-16); ifosfamide; mitoxantrone; vincristine; oxaliplatin; leucovovin; vinorelbine; novantrone; edatrexate; daunomycin; aminopterin; ibandronate; topoisomerase inhibitor RFS 2000; difluoromethylomithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin combined with 5-FU and leucovovin. Other therapeutic agents that may be used in combination with the anti-PD-L1 antibodies of the invention are bisphosphonates such as clodronate, NE-58095, zoledronic acid/zoledronate, alendronate, pamidronate, tiludronate, or risedronate; as well as troxacitabine (a 1,3-dioxolane nucleoside cytosine analog); anti-sense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as Stimuvax vaccine, Theratope vaccine and gene therapy vaccines, for example, Allovectin vaccine, Leuvectin vaccine, and Vaxid vaccine; topoisomerase 1 inhibitor; an anti-estrogen such as fulvestrant; a Kit inhibitor such as imatinib or EXEL-0862 (a tyrosine kinase inhibitor); EGFR inhibitor such as erlotinib or cetuximab; an anti-VEGF inhibitor such as bevacizumab; arinotecan; rmRH; lapatinib and lapatinib ditosylate (an ErbB-2 and EGFR dual tyrosine kinase small-molecule inhibitor also known as GW572016); 17AAG (geldanamycin derivative that is a heat shock protein (Hsp) 90 poison), and pharmaceutically acceptable salts, acids or derivatives of any of the above.

The chemotherapeutic agent can be administered using the appropriate modes of administration, for instance, the modes of administration recommended by the manufacturer. Various routes are utilized to administer the chemotherapeutic agent of the claimed methods, including but not limited to intratumoral, intravenous, intraarterial, intramuscular, subcutaneous, intraperitoneal, aerosol, nasal, via inhalation, oral, transmucosal, transdermal, parenteral, implantable pump or reservoir, continuous infusion, enteral application, topical application, local application, capsules and/or injections. In various embodiments, the chemotherapeutic agent is administered intracranially, intraventricularly, intrathecally, epidurally, intradurally, topically, intravascularly, intravenously, intraarterially, intratumorally, intramuscularly, subcutaneously, intraperitoneally, intranasally, or orally.

In still other embodiments, the expression level of Cdk5 and/or PD-L1 in the cancer cells can be determined prior to administration of the Cdk5 inhibitor and/or other therapeutics. It was found that cell surface expression of PD-L1 and/or upregulation of Cdk5 expression in tumors is a marker for selecting cancer patients who would benefit from treatment with a Cdk5 inhibitor and optionally a PD-L1/PD-1 signaling pathway inhibitor. For example, cell surface expression of PD-L1 and/or expression of Cdk5 in tumors may be used as a marker for identifying or selecting suitable cancer patients who would benefit from immunotherapy with Cdk5 inhibitors and optionally antibodies that target, and disrupt or inhibit signaling from, inhibitory immunoregulators such as PD-L1.

Although the immunotherapy methods described herein including assaying PD-L1 expression and/or Cdk5 expression, are described as comprising the selection of a patient that is, or is not, suitable for Cdk5 ihibitor or as comprising the administration of a Cdk5 inhibitor and optionally a PD-L1/PD-1 signaling pathway inhibitor for immunotherapeutic purposes, it should be understood that these methods apply generally to the selection of a patient that is, or is not, suitable for immunotherapy with, or to the administration of a Cdk5 inhibitor. Further, in any the methods comprising the measurement of PD-L1 and/or Cdk5 expression in a test tissue sample, it should be understood that the step comprising the provision of a test tissue sample obtained from a patient is an optional step. That is, in certain embodiments the method includes this step, and in other embodiments, this step is not included in the method. It should also be understood that in certain preferred embodiments the "assessing" step to identify, or determine the number or proportion of, cells in the test tissue sample that express PD-L1 and/or Cdk5 is performed by a transformative method of assaying for PD-L1 and/or Cdk5 expression, for example by performing a reverse transcriptase-polymerase chain reaction (RT-PCR) assay. In certain other embodiments, no transformative step is involved and PD-L1 expression and/or Cdk5 expression is assessed by, for example, reviewing a report of test results from a laboratory. In certain embodiments, the steps of the methods up to, and including, assessing PD-L1 expression and/or Cdk5 expression provides an intermediate result that may be provided to a physician or other medical practitioner for use in selecting a suitable candidate for Cdk5 inhibitor therapy and/or administering a Cdk5 inhibitor to the patient. In certain embodiments, the steps that provide the intermediate result may be performed by a medical practitioner or someone acting under the direction of a medical practitioner. In other embodiment, these steps are performed by an independent person or laboratory.

The disclosure further provides a method for treatment of a subject afflicted with cancer, which method comprises: (a) selecting a subject that is not suitable for treatment with a Cdk5 inhibitor, the selecting comprising (i) optionally providing a test tissue sample obtained from a patient with cancer of the tissue, the test tissue sample comprising tumor cells and tumor-infiltrating inflammatory cells; (ii) assessing the proportion of cells in the test tissue sample that express PD-L1 and/or Cdk5; and (iii) selecting the subject as not suitable for therapy with a Cdk5 inhibitor, based on an assessment that the proportion of cells in the test tissue sample that express PD-L1 and/or Cdk5 is less than a predetermined threshold level; and (b) administering a standard-of-care therapeutic other than a Cdk5 inhibitor to the selected subject.

In certain embodiments of any of the methods described herein, the proportion of cells that express PD-L1 and/or Cdk5 is assessed by performing an assay to determine the presence of PD-L1 and/or Cdk5 RNA. In further embodiments, the presence of PD-L1 and/or Cdk5 RNA is determined by RT-PCR, in situ hybridization or RNase protection. In other embodiments, the proportion of cells that express PD-L1 and/or Cdk5 is assessed by performing an assay to determine the presence of PD-L1 and Cdk5. In further embodiments, the presence of PD-L1 and/or Cdk5 is determined by immunohistochemistry (IHC), enzyme-linked immunosorbent assay (ELISA), in vivo imaging, or flow cytometry. In preferred embodiments, PD-L1 and/or Cdk5 expression is assayed by IHC.

Imaging techniques have provided important tools in cancer research and treatment. Recent developments in molecular imaging systems, including positron emission tomography (PET), single-photon emission computed tomography (SPECT), fluorescence reflectance imaging (FRI), fluorescence-mediated tomography (FMT), bioluminescence imaging (BLI), laser-scanning confocal microscopy (LSCM) and multiphoton microscopy (MPM), will likely herald even greater use of these techniques in cancer research. Some of these molecular imaging systems allow clinicians to not only see where a tumor is located in the body, but also to visualize the expression and activity of specific molecules, cells, and biological processes that influence tumor behavior and/or responsiveness to therapeutic drugs (Condeelis et al., 2010). Ab specificity, coupled with the sensitivity and resolution of PET, makes immunoPET imaging particularly attractive for monitoring and assaying expression of antigens in tissue samples (McCabe et al., 2010; Olafsen et al., 2010). In certain embodiments of any of the present methods, PD-L1 and/or Cdk5 expression is assayed by immunoPET imaging.

In certain embodiments, the Cdk5 inhibitor can be administered to cancer cells where the surface PD-L1 expression level or Cdk5 expression level exceeds a predetermined threshold value. The predetermined threshold value relating to cell surface PD-L1 expression or Cdk5 expression. The predetermined threshold is based on a proportion of tumor cells in a test tissue sample that expresses PD-L1 and/or Cdk5. In certain embodiments, the predetermined threshold is at least 0.001% of tumor cells expressing PD-L1 and/or Cdk5 as determined by IHC. In other embodiments, the predetermined threshold is at least 0.01%, preferably at least 0.1%, more preferably at least 1% of tumor cells expressing PD-L1 and/or Cdk5, as determined by IHC. In certain embodiments, the predetermined threshold is at least 5% of tumor cells expressing PD-L1 and/or Cdk5 as determined by IHC. In certain embodiments, the predetermined threshold is at least 0.01%, at least 0.1%, at least 1%, or at least 5% of tumor cells expressing s PD-L1 and/or Cdk5 as determined by IHC.

In addition, in any method where administration of a Cdk5 inhibitor is selected or administered based on an assessment that the proportion of cells in a test tissue sample from the subject expresses PD-L1 and/or Cdk5 at a level above a predetermined threshold level, it follows that a complementary method of treatment may be performed wherein a standard-of-care treatment other than the immunotherapy is selected or administered based on an assessment that the proportion of cells in a test tissue sample from the subject expresses PD-L1 and/or Cdk5 at a level below the predetermined threshold level.

This disclosure further provides a method for predicting the therapeutic effectiveness of an Cdk5 inhibitor for treating a cancer patient, which method comprises: (a) optionally providing a test tissue sample obtained from a patient with cancer of the tissue, the test tissue sample comprising tumor cells; (b) assaying the test tissue sample to determine the proportion of cells therein that express PD-L1 and/or Cdk5; (c) comparing the proportion of cells that express PD-L1 and/or Cdk5 with a predetermined threshold value; and (d) predicting the therapeutic effectiveness of the Cdk5 inhibitor in treating the tumor, wherein if the proportion of cells that express PD-L1 and/or Cdk5 exceeds the threshold proportion the Cdk5 inhibitor is predicted to be effective in treating the patient, and wherein if the proportion of cells that express PD-L1 and/or Cdk5 is below the threshold proportion the Cdk5 inhibitor is predicted to not be effective in treating the patient.

The present invention is further illustrated by the following examples which should not be construed as further limiting. The contents of all figures and all references, patents and published patent applications cited throughout this application are expressly incorporated herein by reference.

EXAMPLE 1

In this Example, we explored whether Cdk5 activity plays a role in the in vivo behavior of medulloblastoma (MB), the most common malignant pediatric CNS tumor.

Materials and Methods

Mice

Male B6 nude mice (B6.Cg/NTac-Foxn1nu NE10) were obtained from Taconic, and male C57BL/6J, MHC-II KO and β2M KO mice were obtained from The Jackson Laboratory (Bar Harbor, Me.). NSG mice were obtained from the Athymic Animal and Xenograft Core Facility of the Case Comprehensive Cancer Center. Animals were housed, bred and handled in the Animal Resource Center facilities at Case Western Reserve University according to approved protocols. All animal experiments were performed in 6-12-week old animals with strict adherence to the active experimental protocols approved by the Institutional Animal Care and Use Committee.

Cell Culture

The following cell lines were used in this study: mouse MB cell lines MM1, MM2, MM3 and MMS, derived from Patched$^{+/-}$/p53$^{-/-}$ mice were obtained from G. Plautz (the Cleveland Clinic). Human MB cell lines DAOY, UW228, D283 and D425 were available in our tumor repository. Human RMS cell line SJCRH30 was purchased from ATCC (CRL-2061). Mouse RMS76.9 was generously provided by C. Mackall (NCI/NIH). All cells were grown in RPMI supplemented with 10% FBS.

Cdk5 Gene Silencing in Tumor Cells

Endogenous Cdk5 gene expression in MM1 was silenced using commercially available Cdk5-targeting antisense shRNAs (Thermo Scientific Open Biosystems cat #RMM4532-EG12568) or by designing CRISPR/Cas9 guide RNAs to edit the Cdk5 locus. Antisense GAPDH, or non-silencing shRNA or crNeg constructs were used as controls. Viral particles were generated in HEK293T cells and used to transduce MM1. Gene targeting was validated by western blotting for both shRNA and CRISPR silencing or qPCR in the case of shRNA silencing. For shRNA Cdk5 silencing, a construct with the antisense sequence, TTGAGTAGACAGATCTCCC, afforded 70% gene knockdown relative to wild type and shNS control and was used to generate MM1 shCdk5 cells. CrisprCdk5_92-1 guide RNA with the targeting sequence, GGTCCCTATGTAGCACGTTG, was used to generate MM1 crCdk5 cells.

Western Blot Analysis

Primary antibodies to Cdk5, p35, IRF-1, IRF-2 (Santa Cruz Biotechnology, CA), IRF2BP2 (Abcam, Cambridge, Mass.), HRP secondary antibodies (Cell Signaling Technology, MA) were used for analysis. Whole cell lysates were prepared from mouse and human MB cell lines or other control cells by incubating 4×107 cells in 300 ul of lysis buffer (1% NP-40, 10 mM Tris-HCl, pH7.5, 140 mM NaCl, 2 mM EDTA) supplemented with protease inhibitors (Roche), phosphatase inhibitor cocktails 1 and 2 (Sigma-Aldrich) and Na2VO3 for 30 min on ice followed by centrifugation at 12,000×g for 20 min at 4° C. to remove nuclei and other cell debris. Total protein concentration was determined using the BioRad DC protein assay kit (BioRad cat #500-0116) and the lysates were either used immediately or stored at −80° C. To generate immunoblots, samples were boiled for 5 min at 95° C. in 4× LDS sample buffer containing β-ME, separated on 4-20% Tris-Glycine gels, and the proteins were subsequently transferred onto 0.2 mm nitrocellulose membranes. After blocking for 1 h at RT in 5% non-fat dry milk in 1× TBS/T 0.05%, blots were incubated overnight at 4° C. in primary antibodies to detect target proteins. A blot incubated with anti-beta Actin served as a loading control. After washing (3× for 5 min) in 1×TBS/T, the membranes were incubated for 2 h at RT 20 with a 1:1000 dilution of relevant secondary antibodies followed by SuperSignal West Pico chemiluminescence and bands were visualized using ChemiDoc (BioRad, Inc.).

Flow Cytometric Analysis

Purified or fluorescently labeled antibodies against mouse H-2Kb (clone AF6-88.5), I-Ab (AF6-120.1), PD-1, (clone RMP1-14), PD-L1 (clone 1H5), PD-L2 (clone TY25), FAS-L (clone MFL3), CD80 (clone 16-10A1), CD86 (GL-1), and appropriate secondary antibodies were used as recommended by the manufacture. Briefly, 5×10$^5$ to 1×10$^6$ cells in 100 μl of FACS buffer were incubated staining or isotype-control antibodies on ice in the dark for 45 min. After washing, cells were resuspended in 100 ul of FACS buffer and incubated with 7-AAD for 10 mins for live/dead cell discrimination. Data were acquired immediately by Accuri or FACScaliber and analyzed by FlowJo.

Cdk5 Kinase Activity Assay

Cdk5-specific kinase activity assay was performed using luminescent kinase assay kit as per manufacturer's protocol with slight modifications (Promega). In brief, cell lysates were prepared at 1 µg/µl concentration and precleared with protein Aagarose beads and rabbit IgG (Santa Cruz Biotechnology) at 4° C. for 2 h. An overnight incubation at 4° C. with 5 µg of anti-Cdk5 IgG, followed by 3 h at 4° C. with 25 µl of protein Aagarose beads, immunoprecipitated Cdk5 from the lysates. Immunoprecipitates were washed twice with lysis buffer and twice with kinase buffer [20 mM Tris•HCl (pH 7.4)/10 mM $MgCl_2$/1 mM EDTA/10 µM NaF/1 µM $Na_2VO_3$] and resuspended in 30 µl of water. Ten microliters of kinase assay mixture [100 mM Tris•HCl (pH 7.4)/50 mM MgCl2/5 mM EDTA/50 µM NaF/5 µM Na2VO3/5 mM DTT] and 20 µM NF-H peptide in presence of ATP/ADP-glo mixture and luminescence was measured as readout of correlative kinase activity.

Quantitative PCR Assay

Total cellular RNA was isolated from 5×106-107 cells using TRIZOL and RNAspin Mini kit (GE Healthcare, UK), treated with DNAseI to eliminate genomic DNA, and quantitated using the NanoDrop2000 spectrophotometer. Reverse transcription (RT) of 1 µg of total RNA was performed with oligo(dT)16 using on using SuperScript First Strand Synthesis System for RT-PCR kit (Life Technologies, Carlsbad, Calif.). The resulting cDNA was used as a template for the amplification of target gene transcripts by real time PCR, using SYBR Green PCR Master Mix (Life Technologies, Carlsbad, Calif.) on the ABI 7300 Real-Time PCR machine (Life Technologies, Carlsbad, Calif.). Target gene expression was calculated using the standard curve method upon normalization to cytochrome c housekeeping gene. The primer sequences were as follows: Cdk5 forward: GTCCATCGACATGTGGTCAG; Cdk5 reverse: CTGGTCATCCACATCATTGC; cytochrome c forward: CTGCCACAGCATGGATTATG; cytochrome c reverse: CATCATCATTAGGGCCATCC; p35 forward: GTCCCTATCCCCCAGCTATC; p35 reverse: TTCTTGTCCTTGGCGTTCTT; PD-L1 forward: TGCTGCATAATCAGCTACGG and PD-L1 reverse: TCCACGGAAATTCTCTGGTT.

Genomic Analysis of Cdk5 and PD-L1 Expression in Human Cancers Using UCSC Cancer Genome Browser, cBioPortal, and PrognoScan Cdk5, p35, and p39 mRNA expression was analyzed in pediatric MB and neuroblastoma (NB) samples from the publicly available "Pediatric Tumor Affymetrix Database" of Dr. Javed Khan (Version 2013-09-27; http://pob.abcc.ncifcrf.gov/cgi-bin/JK) accessed through the University of California Santa Cruz Cancer Genomics Browser (https://genome-cancer.ucsc.edu/). Publicly available datasets from The Cancer Genome Atlas (TCGA) including numerous cancer types were accessed from 21 the public access data portal of the Memorial Sloan Kettering Cancer Center cBioPortal (http://www.cbioportal.org/) and analyzed for Cdk5 and PD-L1 (CD274) mRNA expression and mutual exclusivity or co-occurrence of upregulated transcript levels. The results shown are based in part upon data generated through the TCGA Research Network: https://tcgadata.nci.nih.gov/tcga/. Using the PrognoScan database (http://www.prognoscan.org/) and publicly available Gene Expression Omnibus (http://www.ncbi.nlm nih.gov/geo) datasets with the accession numbers GSE 4412-GPL96, GSE19234, GSE22138, GSE68485, GSE4922-GPL96, or the publicly available MGH-glioma data set from the Broad Institute (http://www.broadinstitute.org/cgi-bin/cancer/datasets.cgi), the relationship between Cdk5 expression levels and overall, disease free, or distant metastasis free survival rates were evaluated in glioma, melanoma, breast and lung cancer patients. Patients were stratified into two groups according to their intratumoral Cdk5 expression at various cutoffs, and the cutoff point yielding the most significant survival difference by log-rank test is presented in the Kaplan Meier analysis.

Treatment of MB Cell Lines with Recombinant Mouse IFN-γ (rmIFN-γ)

Murine MB cell lines MM1 WT, MM1 shCdk5 and MM1 shNS were grown in RPMI supplemented with 10% FBS. Once 80% confluent, culture medium was replaced with medium containing 100 ng/ml rmIFN-γ (R&D Systems). Cells were incubated at 37° C. and harvested by incubating for 5 min at 37° C. in 10 mM EDTA/PBS at different time points (0 h, 4 h, 8 h and 24 h). In all subsequent experiments, treatment of cells was carried out for 24 h with 100 ng/ml rmIFN-γ.

Treatment of MB Cell Lines with Roscovitine

Murine MB cell lines MM1 were grown in RPMI supplemented with 10% FBS. A stock solution of Roscovitine (10 mM) or vehicle control-DMSO was diluted in fresh tumor medium and added to samples to achieve a final concentration of 10 µM or 20 µM. After 4 days of treatment, cells were subjected to 100 ng/ml rmIFN-γ (R&D Systems) for 24 hours and then harvested for qPCR analysis.

Tumor Cell Preparation and Injection

For in vivo studies, $5 \times 10^4$ MM1 WT, MM1 shCdk5, or MM1 shNS cells were inoculated s.c. into the left thighs of C57BL/6J or B6 nude mice (B6.Cg/NTac-Foxn2nu NE10). Mice were observed regularly for tumor presence by visual inspection and manual palpation. Tumors were measured using an electronic caliper in the long and short dimensions, and tumor volumes were estimated using the equation: $V=\pi \cdot D \cdot d2$, where D=long dimension and d=short dimension. The mice were typically sacrificed around days 21-28, and the tumor tissues were harvested for weight measurement and further tissue analyses.

IHC Staining

Following approval by University Hospitals Case Medical Center Institutional Review Board, human tissue microarrays were constructed from formalin-fixed and paraffin embedded samples of 6 human MB (4 males, 2 females; age 4-24; classic (2), nodular/desmoplastic (3) and large cell (1) variants), containing 3 cores (2 mm diameter each) per case, and consecutive sections were stained with anti-human Cdk5 (clone 40773, Abcam) and antihuman CD3 (clone 2GV6, Ventana). Expression of Cdk5 was assessed semiquantitatively on a 4-tiered scale as absent, weak, moderate, and strong; the total number of intratumoral CD3+ lymphocytes was counted in 4-5 high-power fields (HPF) and presented as average number of lymphocytes per HPF. For murine samples, $5 \times 10^4$ MM1 shCdk5 or MM1 shNS cells were 22 inoculated into the left thighs or i.c. of C57BL/6 mice. Tumor outgrowths were harvested 2 weeks later, and CD3+ T cell infiltration was assessed by staining with anti-CD3 antibody (clone SP7, Abcam). PD-L1 expression was assessed on serial sections using anti-PD-L1 antibody (clone 28-8, Abcam).

In Vivo Depletion of CD4+ and CD8+ T Cells

To interrogate the role of different T cell subsets in rejecting Cdk5-deficient tumors, we conducted in vivo depletion of T cells in mice prior to and following Cdk5-deficient tumor inoculation. Different groups of mice were injected with 100 ug of anti-CD4 antibody (GK1.5), anti-CD8 antibody (2.43) or both antibodies 72 h and 24 h prior to tumor inoculation and twice weekly thereafter to ensure sustained depletion of T cell subset depletion during the experimental period. One group of mice injected with IgG isotype served as controls. All mice were monitored for development of tumors up to day 25.

Statistical Analysis

Statistical analyses were performed using GraphPad Prism 5 and 6 software (GraphPad Software Inc, San Diego, Calif.). To test for statistical significance, the Student's T-test and two-way analysis of variance with Bonferonni posttests was used to compare between treatment groups. For survival curves log-rank test was used to compare between individual groups. For all analyses $P<0.05$ was considered significant. Results are collective data from 2 to 10 repeat experiments with minimum of 3 mice per experiment.

Phosphoproteomics

Phosphorylation sites were identified based on unbiased phosphopeptide enrichment workflow that couples the immunoprecipitation of phosphorylated peptides with LCMS peak volume quantification. Global phosphorylation studies were performed in MM1 WT cells or MM1 cells with shCdk5 and shNS or crCdk5 and crNeg using an unfractionated label free approach. Cells were lysed in a 2% SDS solution with protease (P845, Sigma Aldrich) and phosphatase (PhosphoSTOP, Roche) inhibitors. Two hundred microliters of cell lysate was washed using the FASP cleaning procedure to remove detergent. All cells were digested with a 2-step Lys C/Trypsin proteolytic cleavage. Samples were then enriched for phosphorylation using $TiO_2$ enrichment spin tips (Thermo Fisher), and subjected to LC-MS/MS using a UPLC system (NanoAcquity) interfaced with an Orbitrap ProVelos Elite MS (Thermo Fisher) for data collection. Rosetta Elucidator software was used to cluster all peptide precursor ions and downstream quantitative modules were used to quantify phosphopeptides. The MASCOT (Matrix Science) protein database was used to identify peptides and proteins. Phosphopeptides with greater than a +/−2-fold change were identified and subjected to One-Way ANOVA analysis to determine statistical significance (p<0.02). Peptides where analyzed with either Ingenuity Pathway Analysis and/or Microsoft Excel.

Results

We explored whether Cdk5 activity plays a role in the in vivo behavior of medulloblastoma (MB), the most common malignant pediatric CNS tumor.

Mouse and human MB cell lines and clinical samples of MB expressed Cdk5 and its coactivators, p35 and p39 (FIGS. 1A, 5A). Cdk5-specific kinase activity could be abolished in vitro by Roscovitine, a non-selective inhibitor against Cdk 1, 2, 5, 7 and 9 currently in clinical trials (FIG. 5B). To further interrogate specific functions of Cdk5 in MB, we disrupted Cdk5 in wild type murine MB cells (MM1 WT) both by short hairpin RNA interference (MM1 shCdk5) and CRISPR/Cas9 targeted mutation (MM1 crCdk5), with scrambled non-silencing (NS) and universal non-targeting constructs as controls (MM1 shNS; MM1 crNeg). A reduction in Cdk5 was confirmed at the transcript level for MM1 shCdk5 (FIG. 5C) and also at the protein level for both MM1 shCdk5 and MM1 crCdk5 (FIG. 1B). In vitro, there were no significant observable differences in cell proliferation among these constructs (FIG. 5D, 5E).

To assess the influence of Cdk5 on MB growth kinetics in vivo, 5×104 Cdk5-deficient or control cells were inoculated subcutaneously (s.c.) into the flanks of NOD/SCID/IL2null mice. All mice developed comparable-sized tumors by day 14 (FIGS. 6A-C). Strikingly, however, when the same tumor cells were inoculated s.c. into naive C57BL/6 mice, 78%-50% of mice injected with Cdk5-deficient MB cells showed tumor-free survival (TFS) at 19 and 42 days, whereas mice injected with the WT and control tumors exhibited 0% and 7% TFS after 19 days, respectively (FIGS. 1C, 7A). Furthermore, mice injected with Cdk5-deficient MB cells developed tumors that were significantly smaller (0.02+/−0.04 g) than those from mice injected with WT (0.91+/−0.39 g) or NS (0.51+/−0.21 g) cells (FIG. 7B). These data suggest a T cell dependent mechanism for rejection of Cdk5-deficient MM1 cells. Supporting this interpretation of our in vivo data, we examined human MB samples and found a significant correlation between low tumor Cdk5 expression and a high number of infiltrating CD3+ T cells (FIGS. 1D; 6D).

To identify specific T cell populations responsible for the potent rejection of Cdk5-deficient MM1 in C57BL/6 mice, we inoculated mice with either MM1 crCdk5 or crNeg cells (5×104 s.c.) and depleted either CD8+ T cells, CD4+ T cells or both subsets using specific depleting antibodies. By day 11, 100% of mice injected with MM1 crNeg and 80% of mice receiving MM1 crCdk5 developed measurable tumors (FIG. 1C), although MM1 crNeg tumors were 8-fold larger than MM1 crCdk5 tumors (808.8+/−382.1 vs. 101.1+/−92.9 mm3; FIG. 1E). Depletion with either αCD4 antibody alone or with both αCD4 and αCD8 antibodies resulted in 4 100% MM1 crCdk5 tumor incidence accompanied by rapid tumor growth, while CD8 depletion alone yielded 30% TFS, similar to isotype control (FIG. 1E) and to NK1.1 depletion (data not shown). Interestingly, 3 of 8 crCdk5-tumor outgrowths among mice injected with IgG2bκ isotype regressed starting on day 17, while 3 of 9 crCdk5 tumor outgrowths among mice depleted of CD8+ T cells regressed starting on day 25, contributing to a total TFS of 50% and 40%, respectively (FIGS. 1C, 1E). Day 42 tumors harvested from MM1 crCdk5-bearing mice remained Cdk5− without evidence of Cdk5+ escape (FIG. 8A). Similar results were seen in mice receiving MM1 shCdk5 and shNS inoculations, with a clear dependency on CD4+ T cells for in vivo tumor rejection (FIG. 7C). In further support of this, Cdk5-deficient tumors grew more aggressively in MHC-II deficient mice compared to MHC-I deficient mice (FIG. 7D). Finally, anti-MM1 immune memory was evident in mice that rejected Cdk5-deficient tumors, as 60-75% of these animals remained tumor free after re-challenge with an otherwise lethal dose of MM1 WT cells (FIG. 7E). Collectively, these studies point to a CD4+ T cell-dependent rejection of Cdk5-deficient tumors with robust anti-tumor immune memory generation.

IFNγ is a major cytokine associated with CD4+ T cell effector function, and IFNγ was abundant in the Cdk5-deficient brain tumor microenvironment (FIG. 2A). IFNγ activates Cdk5 activity by inducting p35. In turn, Cdk5 activates the IFNγ-activated inhibitor of translation (GAIT) complexes. Indeed, Cdk5 kinase activity was significantly increased after 24-hour exposure of MM1 WT and MM1 shNS to IFNγ, whereas MM1 shCdk5 cells showed similar activity as Cdk5$^{-/-}$ embryonic brain tissue (FIG. 2B). IFNγ is known to induce the upregulation of immune checkpoint molecules like PD-L1 in tumor cells, and in infiltrating lymphocytes and monocytes, in a T-cell dependent manner, and the expression of PD-L1 on infiltrating immune cells is evidence of a strong intratumoral immune response. Therefore, we examined whether targeted disruption of Cdk5 expression in MB impaired PD-L1 induction in response to IFNγ stimulation. We first analyzed available human tumor databases and found a co-occurrence of Cdk5 and PD-L1 mRNA expression levels in many tumor types (FIG. 9). Furthermore, in the Cdk5-deficient MM1 we observed a 37.58+/−14.28% reduction in basal PDL1 mRNA level (FIG. 2C). More strikingly, Cdk5-deficient MM1 exhibited a blunted PD-L1 upregulation in response to IFNγ stimulation ex vivo (FIGS. 2C, 2D, 8B). Other IFNγ-responsive proteins were not significantly affected in the Cdk5-deficient tumors, including H-2Kb/Db, FASL, and VCAM-1 (FIG. 10A and data not shown), indicating that a global disruption of the IFNγR signaling pathway was not responsible for the failure of PD-L1 up-regulation in vitro and for the increased T cell immune sensitivity in vivo. Importantly, disruption of Cdk5 in murine and human rhabdomyosarcoma (RMS) cell lines also led to a blunted PD-L1 up-regulation in response to IFNγ stimulation ex vivo (FIGS. 8C-E), indicating that the link between Cdk5 and PD-L1 regulation by IFNγ is not specific only to MB. Time-course analysis revealed that, at 24 hours following IFNγ exposure, surface PD-L1 expression reached a peak of 8.2- and 6.8-fold above baseline in WT and NS cells, respectively (FIG. 2E). The Cdk5-deficient cells only upregulated PD-L1 2.8-fold as compared to baseline, reaching a peak level that was similar to the basal expression in un-stimulated WT and NS controls. The blunted response to IFNγ is specific for PD-L1, as lack of Cdk5 activity did not induce the expression of PD-L2 (FIG. 2F). To further corroborate the link between Cdk5 activity and PD-L1 protein production, we treated MM1 WT cells with Roscovitine and observed a dose-dependent decrease in PD-L1 transcript (FIG. 2G). In addition, in vitro treatment of human MB with Roscovitine diminished surface PD-L1 upregulation upon IFNγ exposure in a dose-dependent manner (FIG. 2H). Stimulation of the WT, 5 NS and Cdk5 deficient cells with TNFα was not accompanied by any differences in PD-L1 upregulation (data not shown). Finally, to establish a functional link between in vivo rejection of Cdk5-deficient MM1 and the failure of these cells to up-regulate surface PD-L1, we disrupted PD-L1 gene (CD274) in MM1 cells (MM1 crPDL1) using CRISPR/Cas9. All of the mice inoculated with MM1 crNeg control cells developed tumors within the first week, while 30% of mice inoculated with MM1 crPDL1 remained tumor free for more than 4 weeks, similar to mice injected with MM1 crCdk5 tumors (FIGS. 2I, 1C).

To further examine the effect of Cdk5 disruption in MB cells, we interrogated key proteins involved in IFNγ signaling. Western blot analysis of Cdk5-deficient and control MM1 cell lysates following IFNγ exposure failed to show any differences between total and phosphorylated (Ser727) forms of STAT1 (FIG. 3A), which correlated with the robust IFNγ induction of MHC class I molecules in Cdk5-deficient MM1 cells (FIG. 10A). To further dissect this STAT1-independent regulation of IFNγR signaling in Cdk5-deficient MM1 cells, we examined the other IFNγ-associated molecules, namely interferon regulatory factor-1 (IRF1) and interferon regulatory factor-2 (IRF2), which have been implicated in the positive and negative regulations of PD-L1 gene transcription, respectively. As expected, IRF1 protein was rapidly induced within 6 hours of IFNγ stimulation and remained elevated for up to 48 hours (FIGS. 3A, 10B). The induction and sustained expression of IRF1 were equivalent in Cdk5-deficient and control MM1 cells, again indicating that proximal IFNγR signaling in Cdk5-deficient cells remained intact. In WT and crNeg cells, the rapid and sustained IRF1 induction was accompanied by a rapid loss of the PD-L1 transcription repressor, IRF2. However, IRF2 and its co-repressor IRF2BP2 were elevated at baseline in Cdk5-deficient cells and persisted for up to 48 hours after IFNγ exposure (FIGS. 3A, 10B). This difference in protein expression cannot be accounted for at the transcriptional level, since Irf2 or Irf2bp2 transcript levels were similar among all cell lines in response to IFNγ stimulation (FIG. 3B). Similarly, STAT2 and STAT3 responded equally to IFNγ among all cell lines (FIG. 10C). Next, we performed phosphoproteomic analysis of both shCdk5 and crCdk5 MM1 cells after 24 hours of IFNγ stimulation. In total, 77 distinct phosphopeptides were identified in the shCdk5 versus WT/shNS screen, and 798 phosphopeptides were identified in the crCdk5 versus WT/crNeg screen. Between these two datasets, a total of 22 proteins were differentially phosphorylated in Cdk5-deficient cells as compared to control cells, with IRF2BP2 being among the highest phosphorylated peptide species associated with IFN signaling pathway in Cdk5-deficient cells (FIG. 3C). These data suggest that persistent IRF2 and IRF2BP2 expression acts to repress PD-L1 transcription, and this functional repression correlates with the hyper-phosphorylation state of IRF2BP2.

Finally, to elucidate the influence of Cdk5 deficiency on MB growth in situ, we introduced Cdk5-deficient MM1 cells orthotopically into the caudal cerebrum of naïve male C57BL/6 mice. Gross inspection revealed a 50% tumor incidence in mice injected with Cdk5-deficient MM1, which mirrors the tumor free survival of subcutaneous Cdk5-deficient tumors; In contrast, 100% of mice injected with WT or NS MM1 cells developed gross brain tumors by day 14 (FIG. 11A). Intracranial (i.c.) Cdk5-deficient tumor outgrowth remained devoid of Cdk5 expression (FIG. 11B) arguing against the tumor outgrowth as a result of Cdk5+ escape variant. Histological analysis showed increased accumulation of PD-L1+ and IBA-1+ cells in the Cdk5-deficient MM1 tumor margin and surrounding stroma (FIG. 4A). Analysis of immune cell 6 composition within the MM1 crCdk5 i.c. tumors showed a modest increase in CD3+ T cells, similar to our observation in the human IHC data (FIGS. 1D, 11C, 11D); however, the percentages of CD3+ cells were equivalent in both crCdk5 and WT tumor samples by flow cytometry (FIG. 4B). Among CD3+ T cells, Cdk5-deficient tumors elicited a significant increased ratio of CD8+ to CD4+ T cell infiltrate with higher PD-L1 expression in both subsets (FIG. 4CE). Although CD8+ T cells are not the primary effector cells responsible for tumor rejection in this model, their increased recruitment in the MB microenvironment reflects an overall inflammatory tumor milieu, as evidence in increased surface PD-L1 expression and overall tissue IFNγ levels (FIGS. 1C, 7C, 2A). A similar phenomenon was also observed in the subcutaneous tumor microenvironment (FIG. 12A-E). Furthermore, the myeloid infiltrate in i.c. tumors shifted from a Ly6C− to a Ly6Chi population with an increased percentage of PD-L1+ cells in bulk CD11b+ cells as well as in each Ly6C subset (FIGS. 4F-H). This was accompanied by a decrease in the observed percentage of microglia (CD11b+CD45lo; FIG. 4F). The Ly6Clo subset expressed a higher density of surface PD-L1 in the Cdk5-deficient tumor microenvironment (FIG. 4H). Again, this finding was recapitulated in subcutaneous tumors, showing a significant increase in the percentage of PD-L1+ cells with a trend towards increased density of PD-L1 staining in the crCdk5 tumor microenvironment (FIG. 12F-I). The observed increase in PD-L1+ populations and staining density aligns with histologic analyses (FIG. 4A, 12B), suggesting a state of global immune activation in response to ongoing IFNγ stimulation. This finding is in good agreement with published reports showing increased PD-L1+ immune cells in MB undergoing immune checkpoint blockade.

Cdk5 has been a focus of anti-cancer therapeutic development in recent years, yet its immune-modulatory role has not been appreciated. Here, we showed conclusively that disruption of Cdk5 sensitizes MB, the most prevalent malignant childhood brain tumor, to CD4+ T cell-dependent immune surveillance. Moreover, we demonstrate this effect is mediated via posttranslational modification of IRF2BP2, leading to the increased abundance of IRF2/IRF2BP2 and sustained functional repression of PD-L1 transcription following IFNγ stimulation. As a key mediator in immunity, IFNγ exhibits both anti-tumor and pro-tumor activities, the latter through production of immunosuppressive molecules such as PD-L1 and indoleamine 2,3-dioxygenase (IDO). IFNγ accomplishes this by binding to the IFNγR1/IFNγR2 heterodimeric receptor, signaling through Jak1 and Jak2, and inducing formation of STAT1 homodimers. STAT1 binds to GAS elements on the promoters of interferon-stimulated genes (ISGs) including IRF1 to induce gene transcription. In turn, IRF-1 activates a multitude of secondary response genes including PD-L1 expression. IRF2 acts as a repressor that competes with IRF1 for binding to the same IRF-E promoter element. Produced constitutively, IRF2 is upregulated in response to either type I IFNs or IRF-1 due to the presence of IRF-E in the IRF2 promoter. Interestingly, while IRF-1 upregulates IRF-2, IRF-2 provides a negative feedback loop by binding to its own promoter to block transcription. The prolonged half-life of IRF-2 (8 hr.) relative to IRF-1 (0.5 hr.) provides a mechanism for the persistence of IRF-2 antagonism. Recently, IRF2BP2 was identified as a co-repressor for IRF-2. Phosphorylation of S-360 on IRF2BP2 is required for nuclear localization of the IRF2-IRF2BP2 complex. Furthermore, low IRF2BP2 expression was correlated with high PD-L1 expression in human breast cancer. Our data suggest a direct link between disruption of Cdk5 expression and activity and the hyper-phosphorylation of IRF2BP2 at sites that are distinct from the known nuclear localization site (data not shown). These novel phosphorylation sites, which are associated with repression of PD-L1 transcription, are distinct from previously described activities of IRF2BP2 on other target 7 genes such as VEGFA or MHC-I. Our data also suggest that Cdk5, either directly or indirectly, inhibits other kinase(s) that can phosphorylate IRF2BP2 (FIG. 13).

Emerging clinical data support the critical role of PD-L1/PD-1 signaling in tumor immune evasion, with roughly 30% of tumors responding to immune checkpoint blockade Immunotherapy approaches targeting the PD-L1/PD-1 pathway have achieved a durable rejection of CNS malignancies in preclinical models. Furthermore, high Cdk5 gene expression is associated with either decreased overall survival or decreased disease free or metastasis free survival in cutaneous melanoma, glioma, breast and lung cancer (FIG. 14), and clinical trials with anti-PD-1/anti-PD-L1 therapy in patients with these cancers are underway. In our studies, both Cdk5- and PD-L1-deficient MB cells exhibit similar TFS (FIGS. 1C, 2I). More CD4+ T cells with lower PD-1 expression were found in the Cdk5-deficient CNS tumor microenvironment, while CD11b+ cells accumulate in larger quantities with higher PD-L1+ expression (FIG. 4C-G). It is unclear whether PD-L1 up-regulation in the myeloid compartment is a response to increasing effector T cell IFNγ production, or if these PD-L1+ myeloid cells play a distinct role modulating the function of infiltrating effector T cells. One such role could be reactivation of tumor-specific CD4+ T cells through cross-presentation of MHC IIassociated tumor antigens, as MM1 cells do not express MHC II molecules (data not shown). Since virtually every human MB contains a CD3+ T cell infiltrate, additional characterization of infiltrating immune cells and manipulation of immune checkpoint may augment clinical efficacy of immunotherapy for MB.

EXAMPLE 2

We performed two in vivo experiments and several repeats of in vitro experiments to assess regulation of PD-L1 expression by tumor cells upon exposure to CYC065 compound in syngeneic mouse Medulloblastoma and Rhabdomyosarcoma cell lines. Results on summarized below:

1) Expression of surface PD-L1 expression on murine tumor cell line models upon exposure to interferon-gamma (IFNγ) in the presence of CYC065.

Experimental Methods a) Seed wild type MM1 (Medulloblastoma) and RMS 76.9 (Rhabdomyosarcoma) tumor cells (100,000 per well in 6-well plate and 3 ml media). Use PD-L1-deficient tumor cells (crPDL1; genetically manipulated using CRISPR-Cas9 technology) as controls:

b) Serum starve overnight c) Add various concentration of CYC065 in DMSO, along with 100 ng/ml IFNγ d) 24 hours later, harvest cells, stain for PD-L1 using anti-mPDL1-PE antibody and analyze by flow cytometry This experiment has been repeated twice with same results. The data showed that at 0.5 µM, MM1 cells began to show PD-L1 down-modulation after 24-hour exposure. At 1 uM, both MM1 and RMS cells completely abrogated their abilities to mount a PD-L1 response upon IFNγ stimulation. This is a >10-fold increase in potency for PD-L1 down modulation as compared to Roscovitin, which shows effects only at 10 µM and above in the same cell lines (reported in Dorand et al. Science 2016; 353:399-403).

2) In Vivo Anti-Tumor Efficacy of CYC065 Against MM1 Tumors:

Experimental Methods e) 10 8-12 week-old C67BL/6 male mice per cohort were used for all in vivo tumor growth kinetics experiment.

f) 50,000 tumor cells were inoculated subcutaneously in the flank on Day 0 g) Starting either Day 0 or Day 7 following tumor inoculation, mice were gavaged with CYC065 compound (dissolved in water) at the highest recommended dose of 50 mg/kg (Cyclacel suggested a dose range of 25-50 mg/kg) using the dosing schedule: daily×5 days with 2 days off.

h) Mice were monitored at least twice a week for tumor growth and tumor size measurements.

i) Tumor mass was resected on Day 21 and grown in culture for 1 week, followed by 24-hour exposure to IFNγ to assess PD-L1 response in vitro.

Interestingly, tumors harvested from in vivo CYC065 treated mice demonstrated reduced PD-L1 response and enhanced MHC-II/MHC-I enhancement upon in vitro exposure to IFNγ, even though CYC065 was no longer present in the tumor culture during the 7-10 culture procedure in vitro. This suggests a potent immune editing and re-wiring of the transcriptomic/translational regulatory pathways in these tumors during their in vivo selection in the presence of CYC065.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of sensitizing medulloblastoma to immunotherapy in a subject in need thereof, comprising:
   detecting the expression level of Cdk5 in medulloblastoma cancer cells of the subject;
   comparing the detected expression level of Cdk5 to a threshold level; and administering to the subject an amount of a CdK5 inhibitor effective to suppress immune checkpoint Programmed Death Ligand (PD-L1) PD-L1 in the cancer cells and to enhance an immune response to the cancer cells, if the detected expression level of Cdk5 exceeds the threshold level.

2. The method of claim 1, wherein the Cdk5 inhibitor is selected from the group consisting of Dinaciclib, AT7519, Roscovitine, CYC065, PHA-793887, Milcidib, and SNS-032.

3. The method of claim 1, further comprising administering a PD-1 binding antagonist and/or a PD-L1 binding antagonist in combination with the Cdk5 inhibitor, the PD-1 binding antagonist and/or a PD-L1 binding antagonist in inhibiting PD-1/PD-L1 interaction.

4. The method of claim 3, wherein the PD-1 binding and/or PD-L1 binding antagonist is an antibody.

5. The method of claim 4, wherein the PD-1 binding antagonist and/or PD-L1 binding antagonist is selected from the group consisting of MDX-1106, Merck 3745, CT-011, AMP-224, AMP-514, YW243.55.S70, MPDL3280A, MDX-1105, MEDI-4736, and MSB0010718C.

6. The method of claim 1, wherein the subject is treated with at least one of tumor removal surgery, chemotherapy, radiation therapy, or immune cells.

7. The method of claim 1, wherein the Cdk5 inhibitor is CYC065.

8. The method of claim 1, comprising detecting the level of PD-L1 in medulloblastoma cancer cells of the subject after administering to the subject the Cdk5 inhibitor.

9. The method of claim 1, wherein the threshold level is at least 1% of medulloblastoma cancer cells expressing Cdk5.

* * * * *